US007176002B2

(12) United States Patent
Lao et al.

(10) Patent No.: US 7,176,002 B2
(45) Date of Patent: Feb. 13, 2007

(54) UNIVERSAL-TAGGED OLIGONUCLEOTIDE PRIMERS AND METHODS OF USE

(75) Inventors: Kai Qin Lao, San Jose, CA (US); Caifu Chen, Palo Alto, CA (US); Ryan T. Koehler, Hayward, CA (US); Charles Scafe, San Francisco, CA (US); Gary Schroth, San Ramon, CA (US)

(73) Assignee: Applera Corporation, Foster City, CA (US)

( * ) Notice: Subject to any disclaimer, the term of this patent is extended or adjusted under 35 U.S.C. 154(b) by 0 days.

(21) Appl. No.: 10/151,061

(22) Filed: May 16, 2002

(65) Prior Publication Data

US 2003/0219751 A1 Nov. 27, 2003

(51) Int. Cl.
*C12P 19/34* (2006.01)
*C07H 21/04* (2006.01)
(52) U.S. Cl. ............... 435/91.1; 435/91.21; 536/24.33
(58) Field of Classification Search .................... 435/6, 435/280, 91.1, 91.2, 91.21; 536/24.3, 23.1, 536/24.32, 24.33; 935/76, 77, 78; 204/182.8; 702/17.2
See application file for complete search history.

(56) References Cited

U.S. PATENT DOCUMENTS

| | | | |
|---|---|---|---|
| 5,470,705 A | 11/1995 | Grossman et al. ............ 435/6 |
| 5,854,033 A | 12/1998 | Lizardi ......................... 435/6 |
| 5,874,215 A * | 2/1999 | Kuiper et al. ................. 435/6 |
| 5,928,907 A | 7/1999 | Woudenberg et al. ..... 435/91.2 |
| 6,154,707 A * | 11/2000 | Livak et al. ................. 702/20 |
| 6,207,372 B1 | 3/2001 | Shuber ......................... 435/6 |
| 6,280,949 B1 * | 8/2001 | Lizardi ......................... 435/6 |
| 6,323,009 B1 | 11/2001 | Lasken et al. ............ 435/91.1 |
| 6,329,175 B1 * | 12/2001 | Conklin et al. .......... 435/69.51 |
| 6,703,228 B1 * | 3/2004 | Landers et al. ........... 435/91.2 |

OTHER PUBLICATIONS

Graber, J. H. et al. In silico detection of control signals: mRNA 3'-end-processing sequences in diverse species. PNAS Nov. 23, 1999, vol. 96, No. 24, 14055-14060.*

Jordan et al. Genome complexity reduction for SNP genotyping analysis. PNAS, vol. 99, No. 5, pp. 2942-2947, Mar. 5, 2002.*

Holland et al. Detection of specific polymerase chain reaction product by utilizing the 5' to 3' exonuclease activity of Thermus Aquaticus DNA polymerase. PNAS, vol. 88, pp. 7276-7280, Aug. 1991.*

Cheung et al., Proc. Natl. Acad. Sci. USA., vol. 93, pp. 14676-14679, Dec. 1996.*

Hawkins et al., Whole genome amplification—applications and advances, *Current Opinion in Biotechnology*, 13(1):65-67 (2002).

Cheung et al., Whole genome amplification using a degenerate oligonucleotide primer allows hundreds of genotypes to be performed on less than one nanogram of genomic DNA, *Proc. Natl. Acad. Sci. U.S.A.*, 93(25):14676-14679.

Barbaux et al., Use of degenerate oligonucleotide PCR (DOP-PCR) for the genotyping of low-concentration DNA samples, *J. Mol. Med.*, 79(5-6):329-332 (2001).

Fortina et al., DOP-PCR amplification of whole genomic DNA and microchip-based capillary electrophoresis., *Methods Mol. Biol.*, 163(2):211-219 (2001).

Talaat et al., Genome-directed primers for selective labeling of bacterial transcripts for DNA microarray analysis, *Nature Biotechnology*, 18:679-682 (2002).

Von Eggeling et al., Applications of random PCR, *Cellular and Molecular Biology*, 41(5):653-670 (1995).

Zhang et al., Whole genome amplification from a single cell: Implications for genetic analysis, *Proc. Natl. Acad. Sci. USA*, 89:5847-5851 (1992).

Jordan et al., Genome complexity reduction for SNP genotyping analysis, *Proc. Natl. Acad. Sci.*, 99(5):2942-2947 (2002).

Venter et al., The Sequence of the Human Genome, *Science*, 291:1304-1351 (2001).

Dean et al., Comprehensive Human Genome Amplification using Multiple Displacement Amplification, *Proc. Natl. Acad. Sci.*, 99(8):5261-5266 (2002).

* cited by examiner

*Primary Examiner*—Kenneth R. Horlick
*Assistant Examiner*—Cynthia B. Wilder
(74) *Attorney, Agent, or Firm*—Knobbe, Martens, Olson & Bear, LLP

(57) ABSTRACT

The present invention relates to universal-tagged oligonucleotide primers, and to methods of using the primers for amplifying the genome.

46 Claims, 7 Drawing Sheets

| 5-mer | C-5-mer | Counts | Frequency (%) |
|---|---|---|---|
| AAAAA | TTTTT | 34196410 | 1.34318 |
| AAAAT | ATTTT | 20414954 | 0.80187 |
| AATA | TATTT | 16864439 | 0.66241 |
| TAAAA | TTTTA | 16839317 | 0.66142 |
| AGAAA | TTTCT | 16045399 | 0.63024 |
| ATAAA | TTTAT | 14223540 | 0.55868 |
| AAATT | AATTT | 14108156 | 0.55415 |
| TTAAA | TTTAA | 13753076 | 0.5402 |
| GAAAA | TTTTC | 13720656 | 0.53893 |
| AATAA | TTATT | 13638528 | 0.5357 |
| CAAAA | TTTTG | 13576003 | 0.53324 |
| AAGAA | TTCTT | 13289245 | 0.52198 |
| AAAGA | TCTTT | 13283223 | 0.52174 |
| AAAAG | CTTTT | 12972403 | 0.50954 |
| AAATG | CATTT | 12214057 | 0.47975 |
| AACA | TGTTT | 12038523 | 0.47285 |
| ACAAA | TTTGT | 12004251 | 0.47151 |
| ATTTA | TAAAT | 11635302 | 0.45702 |
| TGAAA | TTTCA | 11510593 | 0.45212 |
| ATATA | TATAT | 11393381 | 0.44751 |

FIGURE 5 ttgagctgcaggttgaatccgggtgccttaggattcagcaccatggcggaagacatggagaccaaaatcaagaactac aagaccgcccctttgacagccgcttccccaaccagaaccagactgaaactgctggcagaactactggacttccaccg CATGGAGTGctgtcagaaggcaatgaccgctaaaggaggcgatatctctgtgtgcgaatgtgtaccagcgtgtgtaccagtccctgcc COX6b-Fb-U2
(SEQ ID NO: 28)
CATGGAGTGTGTGGCCAGGAGGGATGAGC COX6b-Fa-U2                      Cox6-F58
(SEQ ID NO: 27)                (SEQ ID NO: 32)
TTGGCCAGGAGGTCACAGA     AGCAACGGGCTGAAGGC ccacatcctgggtcacagacTGGGatgagcaacggctgaaggcacgtttcccgggaagatcctgaactggctgcatctcc AGG- GCCCTTCTAGACTTGACCGACGTAGA
                                                             COX6-Probe
                                                            (SEQ ID NO: 34)

cttccttcctgtcctcatccttctcccaggatgtgaaggggacctggtaccagtgatcccacccaggatcctaaa
GAAAGGAGACAGGAGGT    AGAGGGTCCGACGACTCGACCGTGGTGA
Cox6-R58                COX6b-Ra-U1
(SEQ ID NO: 33)     (SEQ ID NO: 29)

tcatgacttacctgctaataaaactcattggaa (SEQ ID NO: 35)

UNIVERSAL-TAGGED OLIGONUCLEOTIDE PRIMERS AND METHODS OF USE

FIELD OF THE INVENTION

The present invention relates to universal-tagged oligonucleotide primers, and to methods of using the primers for amplifying the genome.

INTRODUCTION

Whole genome amplification (WGA) is a valuable technique for amplification of the genome from minimal or limiting amounts of DNA for subsequent molecular genetic analysis. It is desirable that whole genome amplification is conducted to ensure that the amplification is not biased, meaning that all sequences in a sample should be amplified to the same extent.

Whole genome amplification may be performed using either conventional or nonconventional PCR amplification methods. Conventional PCR entails the amplification and subsequent detection of specific DNA sequences which are precisely characterized in length and sequence using non-degenerate primers, while random, "non-conventional" PCR involves universal amplification of prevailing DNA or amplification of unknown intervening sequences which are not generally defined in length or sequence using degenerate primers.

The use of specific primers to amplify genomic DNA (gDNA) is not practical or economical for multiplex applications, such as analyzing single-nucleotide polymorphisms (SNPs), while the use of random primers to amplify gDNA is typically not reproducible or predictable due to non-specific priming.

SUMMARY OF THE INVENTION

In one aspect, the invention provides a method for amplifying target DNA comprising multiple DNA sequences by polymerase chain reaction (PCR) by preparing a mixture of (1) the target DNA, (2) a set of single-stranded oligonucleotide primers, each primer comprising (i) a 3' specific region, (ii) a random region, and (iii) a 5' universal region, wherein the universal region serves as a first universal priming site (U1) for further PCR amplification with a complementary primer, (3) a DNA polymerase, and (4) multiple deoxynucleoside triphosphates (dNTPs) under conditions such that the PCR primers anneal to and prepare a copy of the multiple DNA sequences by primer extension of the target DNA, yielding an amplified product retaining the first universal priming site (U1). The target DNA amplified by this method may be, without limitation, gDNA or cDNA, and may include at least a fraction of the whole human genome. If desired, the amplified product retaining the U1 universal priming site may be further extended to encode a second universal priming site (U2), and further amplified with two primers complementing the first and second universal priming sites (U1 and U2). In one embodiment, the DNA polymerase for amplifying the target DNA is a Taq DNA polymerase, such as, for example, AMPLITAQ GOLD® DNA polymerase, AMPLITAQ® DNA polymerase, or the Stoffel fragment of AMPLITAQ® DNA polymerase. AMPLITAQ GOLD® is a DNA polymerase which is chemically modified to allow for a hot start during PCR. AMPLITAQ® is a DNA polymerase which is recombinantly produced and modified to remove exonuclease activity. If desired, the method of amplifying target DNA may include subjecting the amplified product to single-nucleotide polymorphism (SNP) genotyping. In a particular embodiment, the set of oligonucleotide primers used in the amplification reaction is designed based upon bioinformatic prediction of expected products, using in silico "e-PCR."

In another aspect, the invention provides a universal-tagged single-stranded oligonucleotide primer for polymerase chain reaction (PCR), comprising, (1) a 3' specific region, (2) a random region, and (3) a 5' universal region.

In yet another aspect, the invention provides a set of single-stranded oligonucleotide primers for amplification of genomic DNA (gDNA) in a polymerase chain reaction (PCR), each of the primers comprising (1) a 3' specific region, (2) a random region, and (3) a 5' universal region.

In a further aspect, the invention provides a primer-target duplex that forms between the binding region of the single-stranded oligonucleotide primer and the target DNA.

In all aspects of the invention, the 3' specific region of the oligonucleotide primers may, for example, be about 4 to 12 bases in length. In another embodiment, the 3' specific region may be designed to bind to a genomic sequence occurring in the human genome with a frequency of about 0.01% and 2.00%. In a further embodiment, the random region of the primers may be between about 2 and 15 bases in length. In primers with a random region of 4 bases in length, the sequence of the random region may include all 256 possible combinations of adenosine, cytosine, guanine, and thymidine. In a still further embodiment, the 5' universal region of the primers may be designed to have no significant homology to any segment in the human genome and further to be between about 12 and 35 bases in length.

BRIEF DESCRIPTION OF THE DRAWINGS

FIG. 5 shows a region of the nucleotide sequence of the COX6 gene (SEQ ID NO: 35) with sequences underlined to indicate sites for annealing of primers and probes. The sequence of primers and probes that anneal to the COX6 gene are shown in capital letters directly above the target sequence.

DETAILED DESCRIPTION

A. Definitions

Figure 1:
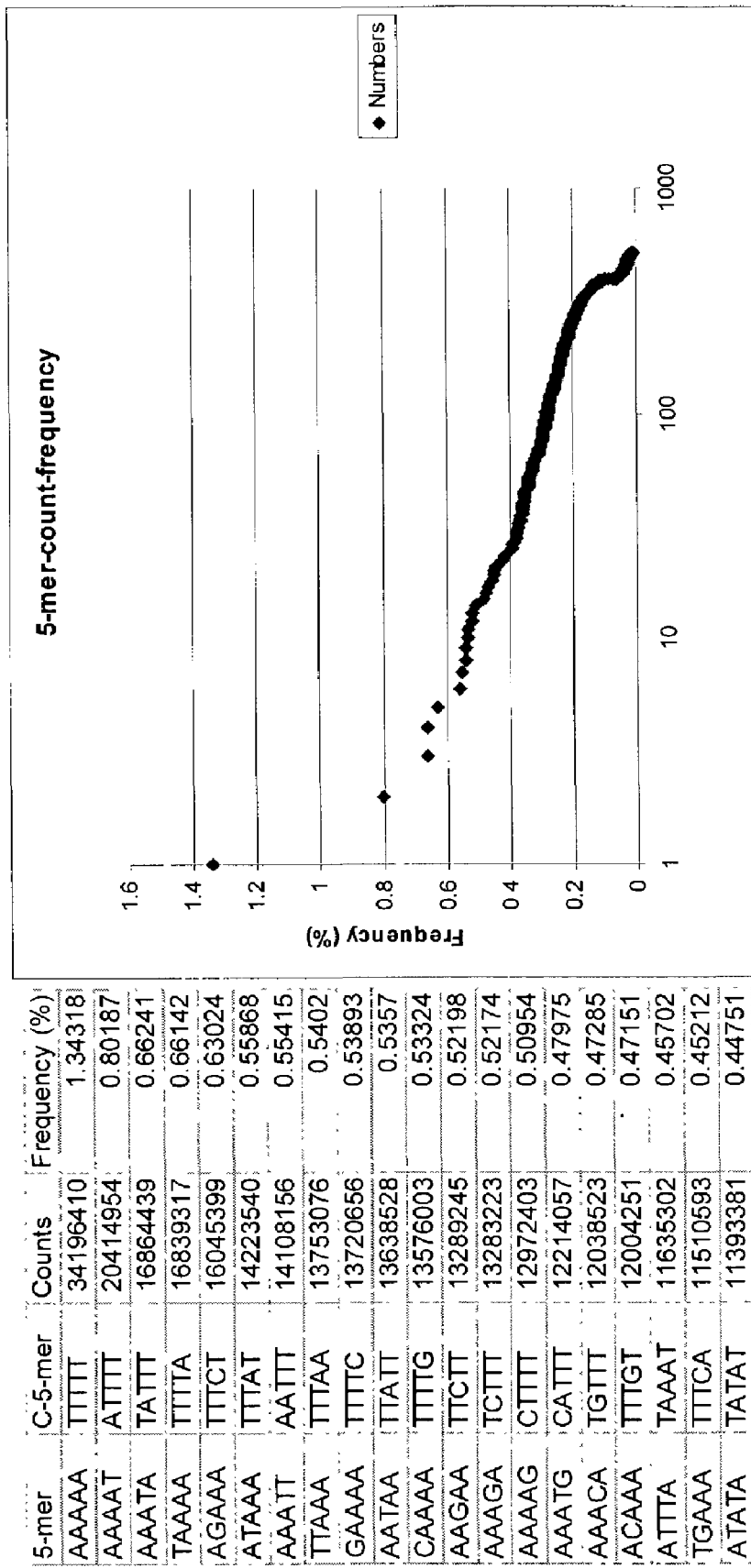
FIG. 1 shows 5-mers that may serve as a specific region in a single-stranded oligonucleotide primer and their frequency of occurrence in the entire human genome.
Figure 2:
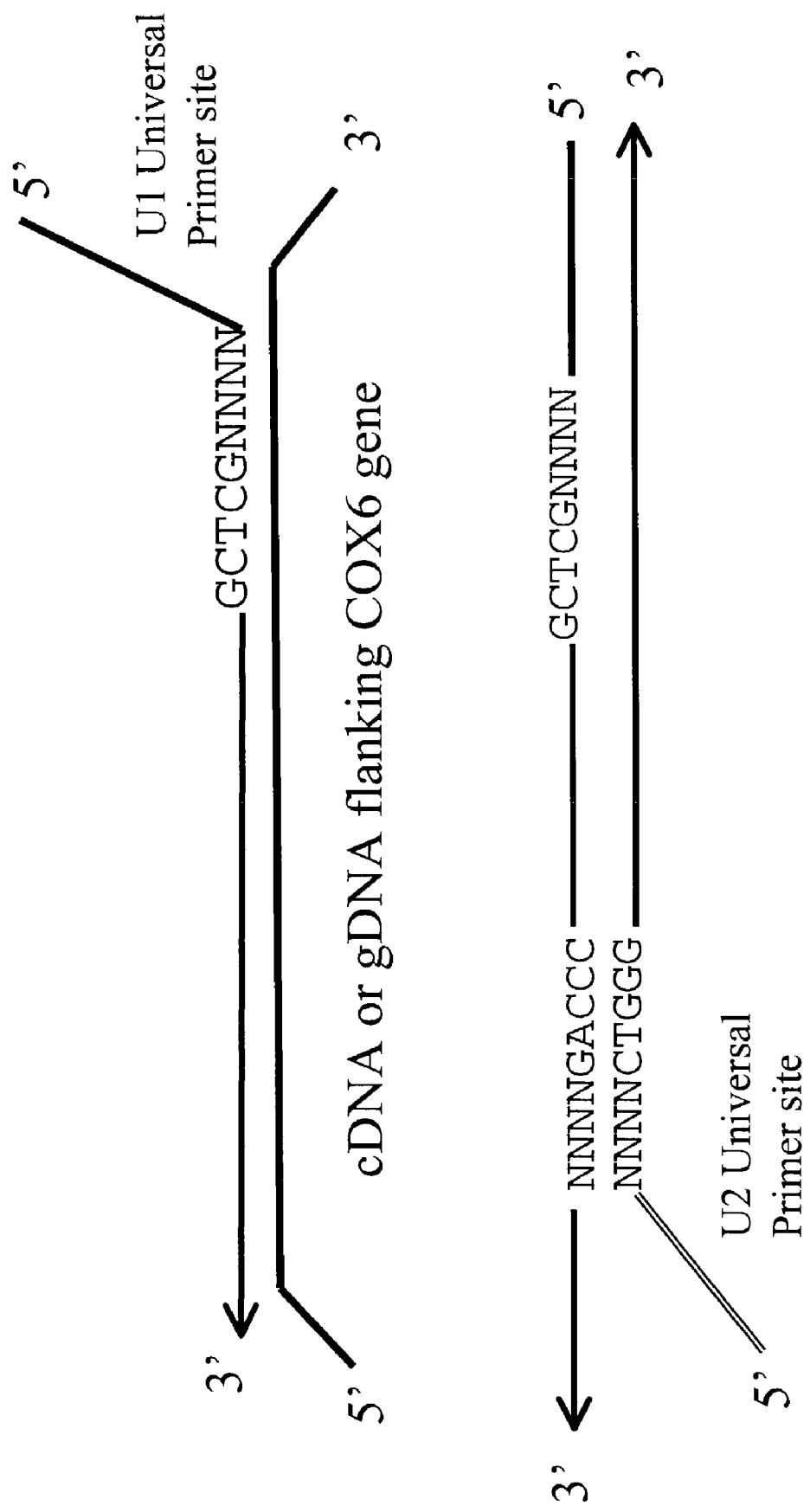
FIG. 2 is a schematic of PCR amplification of the target COX6b DNA sequence using two single-stranded oligonucleotide primers, each having a 3' specific region of 5 bases in length (5'-GCTCG), a random region of 4 bases in length (5'-NNNN), and a 5' universal region (U1 universal primer site or U2 universal primer site) to incorporate a universal U1 and a universal U2 priming site into a PCR-generated copy of the target COX6b DNA sequence.

Unless defined otherwise, technical and scientific terms used herein have the same meaning as commonly understood by one of ordinary skill in the art to which this invention belongs. One skilled in the art will recognize many methods and materials similar or equivalent to those described herein, which could be used in the practice of the present invention. Indeed, the present invention is in no way limited to the methods and materials described. For purposes of the present invention, the following terms are defined below.

"COX6b" when used herein refers to subunit 6b of human cytochrome c oxidase as disclosed, for example, in Taanman et al., *Nucleic Acids Res.*, 17(4): 1766 (1989) and Carrero-Valenzuela et al., *Gene*, 102(2): 229–236 (1991).

As used herein, the terms "polynucleotide" and "oligonucleotide" are used interchangeably and mean single-stranded and double-stranded polymers of nucleotide monomers, including 2'-deoxyribonucleotides (DNA) and ribonucleotides (RNA) linked by internucleotide phosphodiester bond linkages, e.g. 3'-5' and 2'-5', inverted linkages, e.g. 3'-3' and 5'-5', branched structures, or internucleotide analogs. Polynucleotides have associated counter ions, such as $H^+$, $NH_4^+$, trialkylammonium, $Mg^{2+}$, $Na^+$ and the like. A polynucleotide may be composed entirely of deoxyribonucleotides, entirely of ribonucleotides, or chimeric mixtures thereof. Polynucleotides may be comprised of internucleotide, nucleobase and sugar analogs. Polynucleotides typically range in size from a few monomeric units, e.g. 5–40 when they are more commonly frequently referred to in the art as oligonucleotides, to several thousands of monomeric nucleotide units. Unless denoted otherwise, whenever a polynucleotide sequence is represented, it will be understood that the nucleotides are in 5' to 3' order from left to right and that "A" denotes deoxyadenosine, "C" denotes deoxycytosine, "G" denotes deoxyguanosine, and "T" denotes thymidine, unless otherwise noted.

"Nucleotide" refers to a phosphate ester of a nucleoside, as a monomer unit or within a nucleic acid. "Nucleotide 5'-triphosphate" refers to a nucleotide with a triphosphate ester group at the 5' position, and are sometimes denoted as "NTP", or "dNTP" and "ddNTP" to particularly point out the structural features of the ribose sugar. The triphosphate ester group may include sulfur substitutions for the various oxygens, e.g. α-thio-nucleotide 5'-triphosphates. For a review of nucleic acid chemistry, see: Shabarova, Z. and Bogdanov, A. Advanced Organic Chemistry of Nucleic Acids, VCH, New York, 1994.

"Nucleobase" or "base" when used herein refers to any nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases adenine, guanine, cytosine, uracil, thymine, and analogs (Seela, U.S. Pat. No. 5,446, 139) of the naturally occurring nucleobases, e.g. 7-deazaadenine, 7-deazaguanine, 7-deaza-8-azaguanine, 7-deaza-8-azaadenine, inosine, nebularine, nitropyrrole (Bergstrom, J. Amer. Chem. Soc. 117:1201–09 (1995)), nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine (Seela, U.S. Pat. No. 6,147,199), 7-deazaguanine (Seela, U.S. Pat. No. 5,990,303), 2-azapurine (Seela, WO 01/16149), 2-thiopyrimidine, 6-thioguanine, 4-thiothymine, 4-thiouracil, $O^6$-methylguanine, $N^6$-methyladenine, $O^4$-methylthymine, 5,6-dihydrothymine, 5,6-dihydrouracil, 4-methylindole, pyrazolo[3,4-D]pyrimidines, "PPG" (Meyer, U.S. Pat. Nos. 6,143,877 and 6,127,121; Gall, WO 01/38584), ethenoadenine (Fasman (1989) in *Practical Handbook of Biochemistry and Molecular Biology*, pp. 385–394, CRC Press, Boca Raton, Fla.), and locked nucleic acid (LNA).

"Nucleoside" refers to a compound consisting of a nucleobase linked to the C-1' carbon of a sugar, such as ribose, arabinose, xylose, and pyranose, in the natural β or the α anomeric configuration. The sugar may be substituted or unsubstituted. Substituted ribose sugars include, but are not limited to, those riboses in which one or more of the carbon atoms, for example the 2'-carbon atom, is substituted with one or more of the same or different Cl, F, —R, —OR, —$NR_2$ or halogen groups, where each R is independently H, $C_1$–$C_6$ alkyl or $C_5$–$C_{14}$ aryl. Ribose examples include ribose, 2'-deoxyribose, 2',3'-dideoxyribose, 2'-haloribose, 2'-fluororibose, 2'-chlororibose, and 2'-alkylribose, e.g. 2'-O-methyl, 4'-α-anomeric nucleotides, 1'-α-anomeric nucleotides (Asseline (1991) Nucl. Acids Res. 19:4067–74), 2'-4'- and 3'-4'-linked and other "locked" or "LNA", bicyclic sugar modifications (WO 98/22489; WO 98/39352; WO 99/14226). "LNA" or "locked nucleic acid" is a DNA analogue that is conformationally locked such that the ribose ring is constrained by a methylene linkage between the 2'-oxygen and the 3'- or 4'-carbon. The conformation restriction imposed by the linkage often increases binding affinity for complementary sequences and increases the thermal stability of such duplexes.

Exemplary LNA sugar analogs within a polynucleotide include the structures:

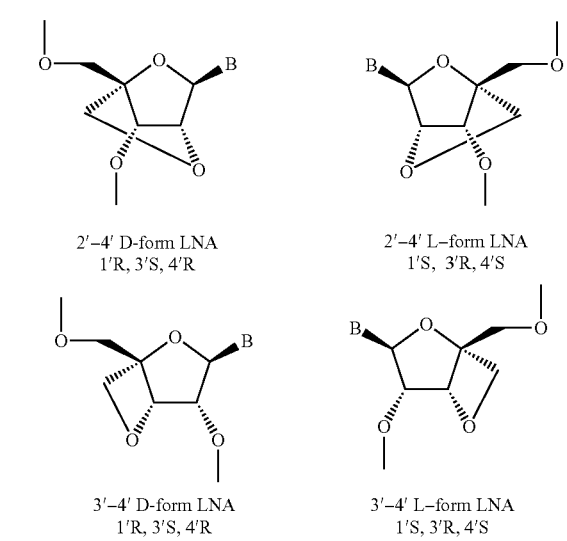

2'–4' D-form LNA
1'R, 3'S, 4'R

2'–4' L–form LNA
1'S, 3'R, 4'S

3'–4' D-form LNA
1'R, 3'S, 4'R

3'–4' L–form LNA
1'S, 3'R, 4'S where B is any nucleobase.

Sugars include modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides include the natural D configurational isomer (D-form), as well as the L configurational isomer (L-form) (Beigelman, U.S. Pat. No. 6,251,666; Chu, U.S. Pat. No. 5,753,789; Shudo, EP0540742; Garbesi (1993) Nucl. Acids Res. 21:4159–65; Fujimori (1990) J. Amer. Chem. Soc. 112: 7435; Urata, (1993) Nucleic Acids Symposium Ser. No. 29:69–70). When the nucleobase is purine, e.g. A or G, the ribose sugar is attached to the $N^9$-position of the nucleobase. When the nucleobase is pyrimidine, e.g. C, T or U, the pentose sugar is attached to the $N^1$-position of the nucleobase (Kornberg and Baker, (1992) *DNA Replication*, $2^{nd}$ Ed., Freeman, San Francisco, Calif.).

"Target", "target polynucleotide", and "target sequence" mean a specific polynucleotide sequence, the presence or absence of which is to be detected, and that is the subject of hybridization with a complementary polynucleotide, e.g. a primer or probe. The target sequence can be composed of DNA, RNA, an analog thereof, and including combinations thereof. The target can be single-stranded or double-stranded. In primer extension processes, the target polynucleotide which forms a hybridization duplex with the primer may also be referred to as a "template." A template serves as a pattern for the synthesis of another, complementary nucleic acid (Concise Dictionary of Biomedicine and Molecular Biology, (1996) CPL Scientific Publishing Services, CRC Press, Newbury, UK). A target sequence for use with the present invention may be derived from any living, or once living, organism, including but not limited to prokaryote, eukaryote, plant, animal, and virus. The target sequence may originate from a nucleus of a cell, e.g., genomic DNA, or may be extranuclear nucleic acid, e.g., plasmid, mitochondrial nucleic acid, various RNAs, and the like. The target nucleic acid sequence may be first reverse-transcribed into cDNA if the target nucleic acid is RNA. A variety of methods are available for obtaining a target nucleic acid sequence for use with the compositions and methods of the present invention. When the target sequence is obtained through isolation from a biological sample, preferred isolation techniques include (1) organic extraction followed by ethanol precipitation, e.g., using a phenol/chloroform organic reagent (e.g., Ausubel et al., eds., (1993) Current Protocols in Molecular Biology Volume 1, Chapter 2, Section I, John Wiley & Sons, New York), or an automated DNA extractor (e.g., Model 341 DNA Extractor, Applied Biosystems, Foster City, Calif.); (2) stationary phase adsorption methods (e.g., Boom et al., U.S. Pat. No. 5,234,809; Walsh et al., (1991) Biotechniques 10(4): 506–513); and (3) salt-induced DNA precipitation methods (e.g., Miller et al., (1988) Nucleic Acids Research, 16(3): 9–10).

Figure 7:
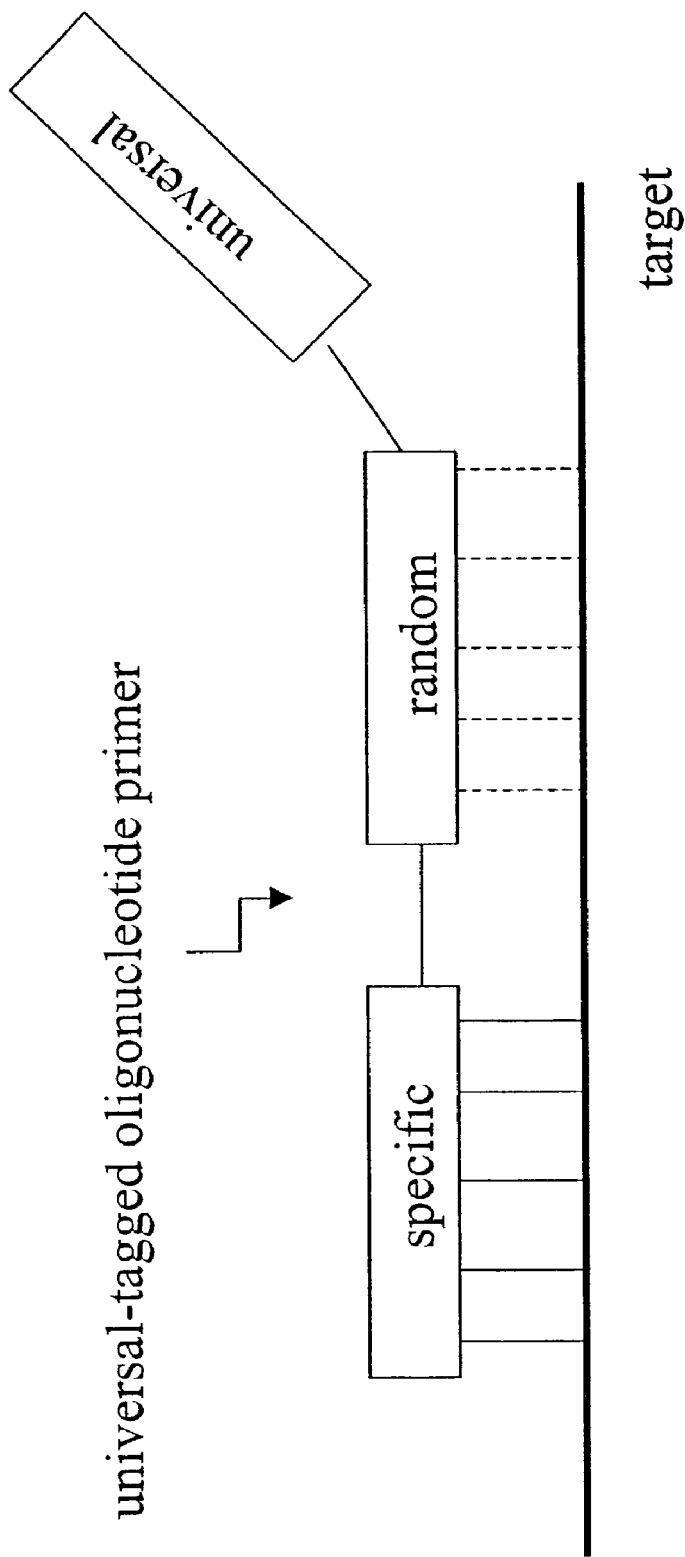
FIG. 7 represents a schematic of the formation of a primer-target duplex between a universal-tagged primer and the target DNA. Vertical solid lines are used to denote complete hydrogen bonding between bases in the specific region of the primer and the target while vertical hatched lines are used to denote less than complete hydrogen bonding between all the bases in the random region of the primer and the target.

The term "primer-target duplex" when used herein refers to the product comprising a region of a primer that is annealed to a target sequence (FIG. 7).

The term "universal region" also referred to as a "5' universal region" or a "universal tag" as used herein refers to a region of an oligonucleotide primer that has no significant homology to any segment in the genome and is localized to the 5' end of the oligonucleotide primer. The "universal region" meets all the requirements for a normal oligonucleotide primer, such as lack of secondary structure, an appropriate Tm, and an appropriate GC content and may be between about 12 and 35 bases in length, between about 15 and 25 bases in length or between about 18 and 22 bases in length. "Universal priming site" when used herein refers to a "universal region" of a primer that may function as a site to which universal primers anneal for priming of further cycles of DNA amplification.

The term "universal primer" as used herein refers to a primer consisting of a "universal region".

The term "universal-tagged oligonucleotide primer" or "universal-tagged primer" when used herein refers to a primer comprising a "5'-universal region", as well as a "3' specific region" and a "random region," unless language to indicate the contrary is specified (FIG. 7). For example, "universal-tagged primer, having a specific binding region" herein refers to a primer of specified sequence, comprising a "universal tag."

The term "specific region" or "3' specific region" as used herein refers to a region of an oligonucleotide primer that is able to anneal to specified sites in the genome. Such a "specific region" is located on the 3'-end of the oligonucleotide primer and is able to bind to a specific genomic sequence occurring in the human genome with a frequency between about 0.01% and 2.0%, such as, for example, between about 0.05% and 0.1% or between about 0.1% and 0.5%. The length of the "specific region" of a primer depends mainly on the averaged lengths of the predicted PCR products based on bioinformatic calculations. The definition includes, without limitation, a "specific region" of between about 4 and 12 bases in length. In more specific embodiments, the length of the 3' specific region may, for example, be between about 4 and 8 bases, or between about 5 and 6 bases. Specific regions having a Tm of between about 50° C. and 70° C. are specifically included within the definition.

The term, "specific primer," when used herein refers to a primer of specified sequence.

The term "random region" as used herein refers to a region of an oligonucleotide primer that is able to anneal to unspecified sites in the genome. The "random region" facilitates binding of the primer to target DNA and binding of the polymerase enzyme used in PCR amplification to the duplex formed between the primer and target DNA. The random region nucleotides may be degenerate or non-specific, promiscuous nucleobases or nucleobase analogs. The length of the "random region" of the oligonucleotide primer, among other things, depends on the length of the specific region. In certain embodiments, without limitation, the "random region" is between about 2 and 15 bases in length, between about 4 and 12 bases in length or between about 4 and 6 bases in length. In another embodiment, the specific and random regions combined will be about 9 bases in length, i.e. if the specific region consists of 4 bases, the random region will have 5 bases.

The term "binding region," unless specified to the contrary, refers to a sequence comprising both a "specific region" and a "random region." A "specific binding region" when used herein refers to a sequence comprising a "specific region," but lacking a "random region."

"Base pair" or "bp" when used herein refers to the association of two complementary nucleotides in a DNA or RNA molecule stabilized by hydrogen bonding.

"GC content" as used herein refers to the percentage of guanine and cytosine bases in a particular oligonucleotide sequence.

"-mer" when used herein refers to a polynucleotide with the number of nucleotides specified immediately prior to "-mer." For example, "5-mer" refers to a polynucleotide consisting of 5 bases.

"Primer" means an oligonucleotide sequence that is designed to hybridize with a complementary portion of a target sequence, a probe, or a ligation product, and undergo primer extension. A primer functions as the starting point for the polymerization of nucleotides (Concise Dictionary of Biomedicine and Molecular Biology, (1996) CPL Scientific Publishing Services, CRC Press, Newbury, UK).

The term "degenerate primer" when used herein refers to a mixture of similar primers with differing bases at the varying positions (Mitsuhashi M, *J Clin Lab Anal*, 10(5): 285–93 (1996); von Eggeling et al., *Cell Mol Biol*, 41(5): 653–70 (1995); (Zhang et al., *Proc. Natl. Acad. Sci. USA*, 89:5847–5851 (1992); Telenius et al., *Genomics*, 13(3): 718–25 (1992)). Such primers may include inosine as inosine is able to base pair with adenosine, cytosine, guanine or thymidine. Degenerate primers allow annealing to and amplification of a variety of target sequences that may be related. Degenerate primers that anneal to target DNA may function as a priming site for further amplification.

The term "probe" when used herein refers to a polynucleotide that is capable of forming a duplex structure by complementary base pairing with a sequence of a target polynucleotide. For example, probes may be labeled, e.g. with a quencher moiety, or an energy transfer pair comprised of a fluorescent reporter and quencher.

The term "set" when used herein refers to a multiplicity of primers. The minimum number of primers comprised within a set depends on the intended application, and may be determined based upon principles well known in the art, such as by using computer-based methods. An exemplary "set" may, for example, comprise between about 2 and 20 primers but the use of sets comprising more than 20 primers is also contemplated.

The terms "duplex" means an intermolecular or intramolecular double-stranded portion of a nucleic acid which is base-paired through Watson-Crick, Hoogsteen, or other sequence-specific interactions of nucleobases. A duplex may consist of a primer and a template strand, or a probe and a target strand. A "hybrid" means a duplex, triplex, or other base-paired complex of nucleic acids interacting by base-specific interactions, e.g. hydrogen bonds.

The term "anneal" as used herein refer to the base-pairing interaction of one polynucleotide with another polynucleotide that results in the formation of a duplex or other higher-ordered structure. The primary interaction is base specific, i.e., A/T and G/C, by Watson/Crick and Hoogsteen-type hydrogen bonding.

The term "primer extension" means the process of elongating a primer that is annealed to a target in the 5' to 3' direction using a template-dependent polymerase. According to certain embodiments, with appropriate buffers, salts, pH, temperature, and nucleotide triphosphates, including analogs and derivatives thereof, a template dependent polymerase incorporates nucleotides complementary to the template strand starting at the 3'-end of an annealed primer, to generate a complementary strand.

"Amplification" of a nucleic acid, as used herein, denotes the use of polymerase chain reaction (PCR) to increase the concentration of a particular DNA sequence within a mixture of DNA sequences. An "amplicon" is a target DNA sequence that is amplified by PCR.

The term "real-time analysis" refers to periodic monitoring during PCR. Certain systems such as the ABI 7700 and 7900HT Sequence Detection Systems (Applied Biosystems, Foster City, Calif.) conduct monitoring during each thermal cycle at a pre-determined or user-defined point. Real-time analysis of PCR with FRET probes measures fluorescent dye signal changes from cycle-to-cycle, preferably minus any internal control signals.

"5'-nuclease analysis" or "5'-nuclease assay" when used herein refers to "real-time analysis" for quantification of the amount of DNA amplified in a particular PCR reaction. TAQMAN® analysis is an example of such "5'-nuclease analysis". (a commercially available PCR kit). "5'-nuclease analysis" involves the use of a fluorogenic oligonucleotide probe to which a reporter dye and a quencher dye are attached. During amplification of a nucleotide sequence using a forward and reverse primer, the probe anneals to the target of interest between the forward and reverse primer sites. During extension, the probe is cleaved by the 5'-nuclease activity of the DNA polymerase. As the cleavage separates the reporter dye from the quencher dye, the reporter dye's fluorescence increases which may be detected and quantitated. Real-time analysis of PCR with 5'-nuclease assay involves FRET probes that may be displayed by plotting the logarithmic change in detected fluorescence (ΔRn) versus the cycle number. The cycle within the PCR protocol at which the change in fluorescence (ΔRn) rises above a threshold value is denoted as $C_T$. The $C_T$ cycle is approximately the cycle at which amplification of target becomes exponential. A relatively low $C_T$ value indicates efficient detection of amplicon. The threshold cycle is highly correlated to the amount of copy number, or amount of target polynucleotide present in the sample, as well as the efficiency of amplification. The effects of primer constitution, e.g. length, sequence, mismatches, analogs, can be conveniently screened and quantitated by measurement of $C_T$ values during real-time analysis of PCR.

"FRET" when used herein refers to fluorescence resonance energy transfer, a quantum mechanical phenomenon that occurs between a fluorescence acceptor and a fluorescence donor. For example, the TAQMAN® PCR assay is a method that utilizes oligonucleotide probes that are labeled at each end with a fluorescence donor and acceptor pair and undergo FRET in their intact state. The probe is designed to hybridize to a sequence being amplified in a PCR reaction using a polymerase. If a duplex forms between the probe and the target, the 5'-exonuclease activity of the Taq polymerase, from *Thermus aquaticus*, is able to digest the hybridized TAQMAN® probe during the elongation cycle, separating the donor from the acceptor and resulting in a decrease in FRET and an increase in emission of fluorescence from the fluorescence donor.

"Polymerase chain reaction" or "PCR" as used herein, refers to a method well-known in the art for amplification of a nucleic acid. The method involves introducing a molar excess of two or more extendable oligonucleotide primers to a reaction mixture comprising the desired target sequence(s), where the primers hybridize to opposite strands of the double stranded target sequence. The reaction mixture is subjected to a precise program of thermal cycling in the presence of a DNA polymerase, resulting in the amplification of the desired target sequence flanked by the oligonucleotide primers. The oligonucleotide primers prime multiple sequential rounds of DNA synthesis, each round of synthesis is typically separated by a melting and re-annealing step. Methods for a wide variety of PCR applications are widely known in the art, and are described in many sources, for example, Ausubel et al. (eds.), *Current Protocols in Molecular Biology*, Section 15, John Wiley & Sons, Inc., New York (1994).

"In silico e-PCR" when used herein refers to a computer-conducted method for predicting the size and probability of amplification of a nucleotide sequence using a particular set of primers. The method involves searching a DNA database for exact matches to the primer sequences and further for sequences having the correct order, orientation, and spacing to allow priming of amplification of a nucleotide sequence of a predicted size.

"Single Nucleotide Polymorphism" or "SNP" when used herein refers to a variation in a single nucleotide in a genomic sequence. In one embodiment, such "SNP"s may be functionally significant and may play a role in susceptibility to disease.

"SNP genotyping" when used herein refers to detecting whether a particular SNP is present in a DNA sample isolated from a particular cell or individual.

"Tm" as used herein, refers to the melting temperature (temperature at which 50% of the oligonucleotide is a duplex) of the oligonucleotide calculated using the nearest-neighbor thermodynamic values of Breslauer et al. (*Proc. Natl. Acad. Sci. USA* 83:3746–3750, 1986) for DNA and Freier et al. (*Proc. Natl. Acad. Sci. USA* 83:9373–9377, 1986) for RNA.

"Stoffel fragment" when used herein refers to an enzyme that is a modified form of recombinant AMPLITAQ® DNA Polymerase. This enzyme is more thermostable than AMPLITAQ® DNA Polymerase, is active over a 2 mM–10 mM range of magnesium iron concentration, and lacks 5'-3' exonuclease activity. "Genomic DMA" or "gDMA" refers to all the DMA sequences comprising the entire genome of an organism.

"Complementary DNA" or "cDNA" when used herein refers to a DNA copy of a mRNA. Such "cDNA" lack introns present in genomic DNA.

"Messenger RNA" or "mRNA" when used herein refers to RNA that specifies the order of amino acids in protein synthesis.

The term "end-point analysis" refers to a method where data collection occurs only when a PCR reaction is substantially complete.

The term "significant homology" when used herein means perfect complementarity between bases or alternatively, no more than 1 or 2 mismatches of bases.

B. Universal-Tagged Primer Design

Based on knowledge of the sequences of entire genomes, it is possible to compute the minimal number of primers needed to amplify all the genes within a particular genome. For example, such genome-directed primer strategies predicted that 37 primers (7-mers or 8-mers) were able to prime the 3,924 genes in the Mycobacterium tuberculosis genome (Talaat et al., *Nature Biotech.*, 18:679–682 (2000)). In addition, the completion of the approximately 3 billion base pairs sequence of the human genome enables the design of primers based on whole-genome scale instead of a random approach.

The present invention provides a sequence-directed strategy to amplify fractions of the entire genome, including the whole human genome. This strategy involves the design of primers (FIG. 7) comprising the following regions: (1) a specific region (typically about 5 bases long), (2) a random region (typically about 4 bases long), and (3) a universal region (typically about 18 bases long). The specific region, which is located on the 3'-end of the primer, can anneal to many specified sites in the genome. The random region helps to facilitate binding of the primer to target DNA and binding of the polymerase enzyme used in PCR amplification to the priming site. The universal region is a priming site for further PCR amplification with a complementary primer. The role of each region in the PCR amplification process will be described in greater detail below.

In general PCR primers are designed using a core set of parameters, such as primer length, melting temperature ($T_m$), GC content, complementarity to optimize the PCR products, primer bending and folding, weighting these and similar parameters to different degrees depending on the specific task.

Since both specificity, and the temperature and time of annealing are at least partly dependent on primer length, the total length of the primers is critical for the successful performance of the PCR amplification reaction. In general, longer primers are typically less efficient than shorter primers. Accordingly, this is taken into account when determining the length of the individual regions within the primers herein. In general, the total length of the primers may be between about 18 bases and about 65 bases, such as, for example, between about 23 and 45 bases or between about 27 and 34 bases.

In the primers of the present invention, the specific region is designed to specifically bind short sequences occurring with high frequency in the genome to be amplified. The length of the specific region depends mainly on the averaged lengths of the predicted PCR products based on bioinformatic calculations. In general, the longer the specific region is, the more primers are needed to amplify the same number of regions of the genome, because longer specific regions are more rare and typically are spaced farther apart. Thus, based upon stability and efficiency of duplex formation, the use of a sequence-specific region of about 9 bases would appear ideal. However, unique sequences of 9 bases in length are rare in the genome, therefore, the amplification of the same number of regions of the genome, using primers with specific regions of 9 bases would require more primers than the same amplification using primers with shorter specific regions. In order to determine the frequency of 5-mers in the whole human genome, the occurrence of all 1024 possible 5-mers were counted. The results are shown in FIG. 1. For the top 50 most frequent 5-mers (Table 1), the average distance between a given 5-mer is about 200–500 bp. In addition, when one of the top 20 most frequent 5-mers and 6-mers in the human genome are used for amplification of the human genome, bioinformatic calculations show that the amplified products average 74–523 bps. Thus, primers with specific regions less than 9 bases are contemplated. Based on the foregoing considerations, the primers of the present invention specifically include specific regions of between about 4 and 12 bases in length, although the use of primers with longer or shorter specific regions, for example between about 4 and 8 bases in length or between about 5 and 6 bases in length is also contemplated. When the specific region is 5 bases in length, the sequence of the 3' specific region may be selected from the group consisting of the primers listed in Table 1.

The random region is used to adjust the performance of the primer, both in terms of thermodynamics of the primer binding to the target (e.g., $T_m$ of primer), and an expected stabilizing effect of having a longer duplex for the polymerase enzyme to bind. The length of the random region of the primer depends on the length of the specific primer and the fact that the minimum duplex required for good enzyme activity is expected, as mentioned above, to be about 9 bases, but also depends on the presence of high $T_m$ nucleobase analogs. The random region may be between about 2 and 15 bases in length, between about 4 and 12 bases in length or between about 4 and 6 bases in length. A duplex of such length also provides the primer with a favorable thermal melting temperature ($T_m$). Thermal melting, $T_m$, values were estimated for DNA primers and DNA probes by calculations using the basic formula: $T_m=81.5+16.6(\log_{10}[Na^+])+0.41(\%G+C)-(600/N)$, where N=oligonucleotide length in number of nucleotides (Bolton et al., *Proc. Natl.*

Figure 6:
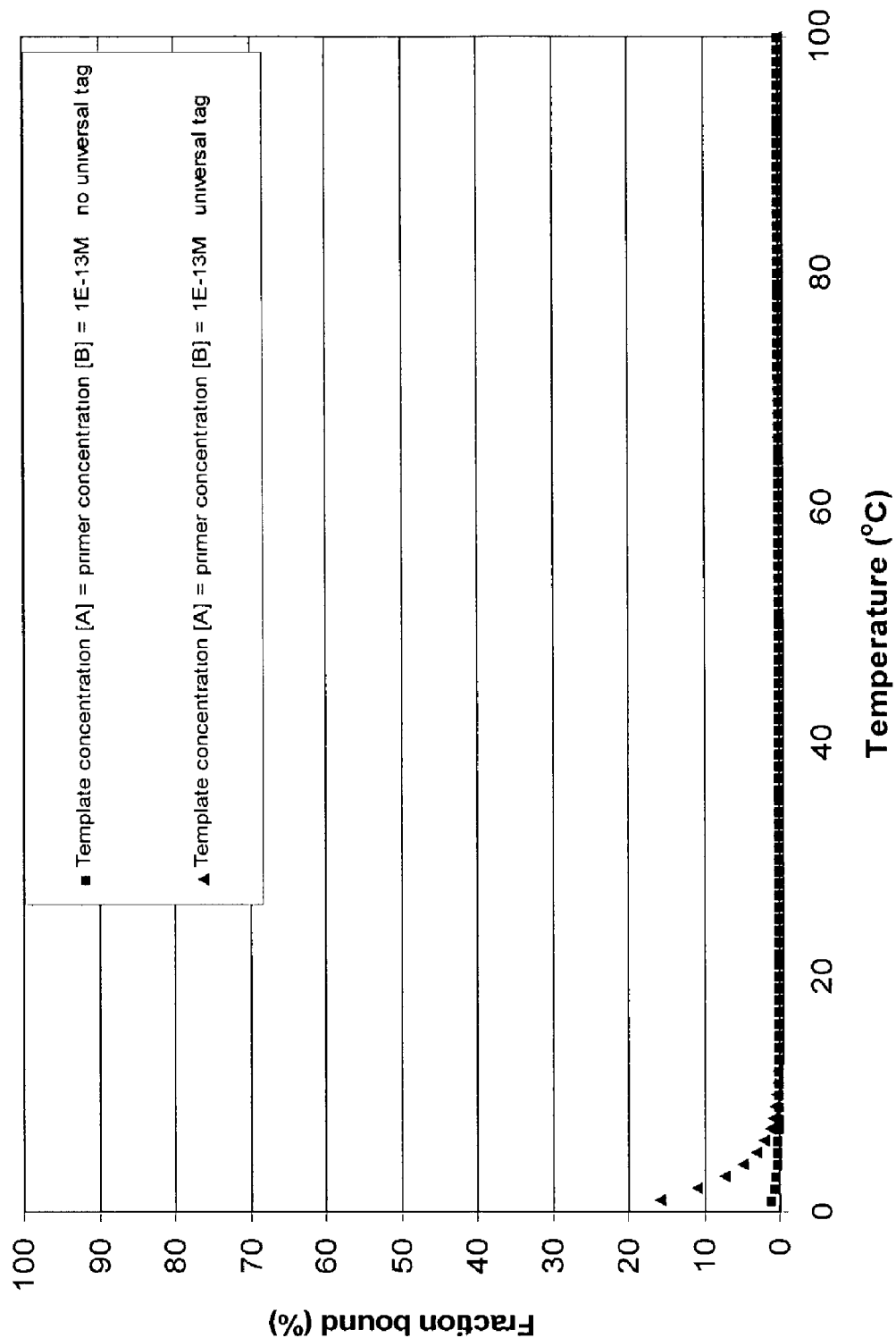
FIG. 6 shows the Tm calculation for the formation of duplexes between target DNA and primers either with or without a universal tag.

Acad. Sci., 48:1390 (1962); Sambrook et al., *Molecular Cloning, A Laboratory Manual, Second Edition*, pgs. 2:11.46, 9.50–9.51, (1989). Refinements to the basic formula may be made for nearest-neighbor and solvent effects (Blackburn and Gait (editors), "DNA and RNA structure," *Nucleic Acids in Chemistry and Biology*, 2$^{nd}$ edition, Oxford University Press, pgs. 70–71 (1996); Breslauer et al., *Proc. Natl. Acad. Sci. USA*, 83:3746–50 (1986)). In calculations done using a current nearest-neighbor model (FIG. 6), this length of primer will have an average $T_m$ of about 20° C. for a 9-mer (with a universal region under typical buffer conditions). However, even with such a low $T_m$, the predicted fraction of the duplex formed at higher temperatures is not zero. In fact, at 50° C., where the polymerase enzyme has high activity, there is still a small fractional amount of hybridized primer (about 0.1 to 1% at high, e.g. mM, primer concentrations). Accordingly, in primers containing a 5 base specific region, the random region may be about 4 bases, although longer or shorter random regions are contemplated. When the random region is 4 bases in length, the sequence is selected from all possible combinations of A, C, T and G bases. Preferably, such random regions do not include combinations occurring in the genome with high frequency.

The universal region of the primer is designed to have no significant homology to any segment in the genome and serves to function as sites to which universal primers anneal for future cycles of amplification. The universal region must meet all the requirements for a normal PCR primer, such as a lack of secondary structure, an appropriate Tm (typically between about 55 and about 65° C.) and appropriate GC content (typically about 40–60%). The sequence of the 5' universal region may, for example, be selected from the group consisting of: AGTGGTGCCAGCTCAGCAG (SEQ ID NO: 1) CATGGAGTGTTGGCCAGGA (SEQ ID NO: 2), AACTCTCTCCCAAGAGCGA (SEQ ID NO: 3); TAGCGTAGTGAGCATCCGT (SEQ ID NO: 4); TCCCACATTCACCGCTTAG (SEQ ID NO: 5); TGTAAAACGACGGCCAGT (SEQ ID NO: 6); and GTACGCAGTCTACGAGGC (SEQ ID NO: 7). The length of the universal region will be affected by the lengths of the specific and random regions, and the total length of the primer. The length may be between about 12 and 35 bases in length, between about 15 and 25 bases in length or between about 18 and 22 bases in length. Typically, the whole primer, including the universal region (providing a universal priming site) may be between about 18 bases and about 65 bases, between about 23 and about 45 bases or between about 27 and about 34 bases.

The primers of the invention may include locked nucleic acid (LNA) bases. LNA are modified DNA analogs, which obey Watson-Crick base pairing and Hoogsten triplex formation rules, and have improved hybridization characteristics and biostability (see, e.g., Singh et al., *Chem. Commun.* 455–456 (1998); Koshkin et al., *Tetrahedron* 54:3607–3630 (1998)). Under appropriate conditions, and with careful primer design, LNA bases can increase Tm, and improve the efficiency of nucleic acid amplification.

TABLE 1

50 Most Frequent 5-mers in the Human Genome

| 5-mer | C-5-mer | Counts | Frequency (%) |
|---|---|---|---|
| AAAAA | TTTTT | 34196410 | 1.34318 |
| AAAAT | ATTTT | 20414954 | 0.80187 |
| AAATA | TATTT | 16864439 | 0.66241 |

TABLE 1-continued

50 Most Frequent 5-mers in the Human Genome

| 5-mer | C-5-mer | Counts | Frequency (%) |
|---|---|---|---|
| TAAAA | TTTTA | 16839317 | 0.66142 |
| AGAAA | TTTCT | 16045399 | 0.63024 |
| ATAAA | TTTAT | 14223540 | 0.55868 |
| AAATT | AATTT | 14108156 | 0.55415 |
| TTAAA | TTTAA | 13753076 | 0.5402 |
| GAAAA | TTTTC | 13720656 | 0.53893 |
| AATAA | TTATT | 13638528 | 0.5357 |
| CAAAA | TTTTG | 13576003 | 0.53324 |
| AAGAA | TTCTT | 13289245 | 0.52198 |
| AAAGA | TCTTT | 13283223 | 0.52174 |
| AAAAG | CTTTT | 12972403 | 0.50954 |
| AAATG | CATTT | 12214057 | 0.47975 |
| AAACA | TGTTT | 12038523 | 0.47285 |
| ACAAA | TTTGT | 12004251 | 0.47151 |
| ATTTA | TAAAT | 11635302 | 0.45702 |
| TGAAA | TTTCA | 11510593 | 0.45212 |
| ATATA | TATAT | 11393381 | 0.44751 |
| AATAT | ATATT | 11353367 | 0.44594 |
| AAAAC | GTTTT | 10747752 | 0.42216 |
| AGAGA | TCTCT | 10693461 | 0.42002 |
| AATTA | TAATT | 10254452 | 0.40278 |
| AGGAA | TTCCT | 9935310 | 0.39024 |
| AACAA | TTGTT | 9923966 | 0.3898 |
| CCCAG | CTGGG | 9871598 | 0.38774 |
| TCAAA | TTTGA | 9698717 | 0.38095 |
| ATTTC | GAAAT | 9622174 | 0.37794 |
| ATAAT | ATTAT | 9603349 | 0.3772 |
| ACACA | TGTGT | 9546388 | 0.37497 |
| CAGAA | TTCTG | 9465179 | 0.37178 |
| AGAAT | ATTCT | 9299112 | 0.36526 |
| GAGAA | TTCTC | 9286534 | 0.36476 |
| GGAAA | TTTCC | 9272767 | 0.36422 |
| TCCCA | TGGGA | 9183471 | 0.36071 |
| ATTAA | TTAAT | 9159692 | 0.35978 |
| ATGAA | TTCAT | 9130836 | 0.35865 |
| AAAGT | ACTTT | 9098500 | 0.35738 |
| AATGA | TCATT | 9095115 | 0.35724 |
| TTCAA | TTGAA | 9016495 | 0.35415 |
| ATTTG | CAAAT | 8987366 | 0.35301 |
| TCTCA | TGAGA | 8981902 | 0.3528 |
| ACAGA | TCTGT | 8979579 | 0.3527 |

C. Use of Universal-Tagged Primers to Amplify Fractions of the Genome

Practical issues hinder the amplification of all 3 billion base pairs of a whole genome in a single PCR reaction. Such limitations include the availability of primers and dNTPs, and the total amount of DNA that can be amplified in a single tube. For example, with 2 mM dNTPs in a 100 µl volume, one PCR reaction can make about 1.6×10$^8$ copies of the genome which is about 2.7 pM of the genomic DNA (gDNA). To form 1.5×10$^7$ fragments with the average size of 200 base pairs, the reaction needs 2.4×10$^{15}$ pairs of primers to make 1.6×10$^8$ copies for each using approximately a primer concentration of 40 µM in each 100 µL PCR reaction.

Figure 3:
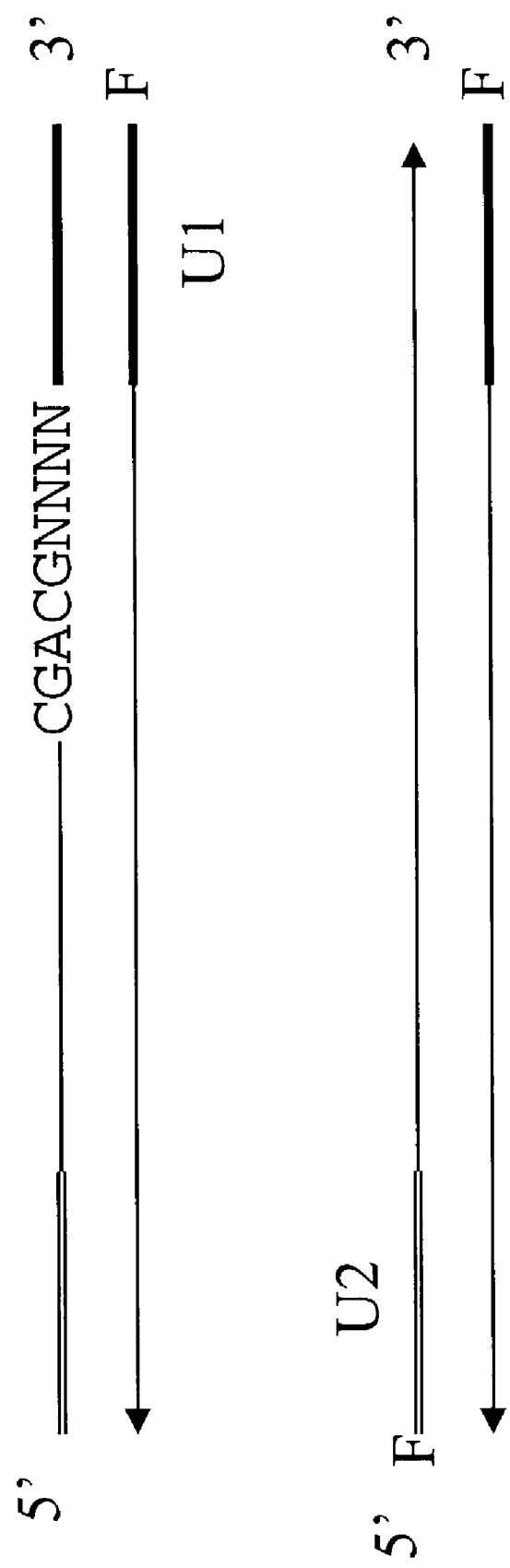
FIG. 3 is a schematic of the use of U1 and U2 primers to further amplify a PCR-generated copy of target DNA containing a universal U1 and universal U2 priming site.

Because of the practicality limitations, a more feasible approach is to amplify partial regions of the whole genome using a set of primers designed as discussed above, for example a set of primers including a sequence-specific region, a random region, and a universal adapter region (universal tag) (FIG. 7). Such primers will be briefly referred to as universally tagged primers. In silico "e-PCR" (Schuler, G. D., *Genome Res*, 7(5):541–50 (1997); Schuler, G D, *Trends Biotechnol*, 16(11):456–9 (1998)) of gDNA may be used to predict the product, expected size of the product, and probability of amplifying a particular region of the genome with a set of such primers in a particular PCR reaction. Accordingly, primer sets can be pooled based on such computer-based in silico "e-PCR" of gDNA. A possible format is to first amplify the whole genome in separate PCR reactions in a 96-well plate, with each well containing selected primer sets designed as discussed above, such as universally tagged primer sets. The amplified products can then be further amplified with the two universal primers that are complementary to the universal priming sites, i.e. U1 or U2, of the universal-tagged primers (FIG. 3), e.g. 9-mers.

1. Efficiency of Amplification

In one embodiment of the invention, the efficiency of amplification of sequences from gDNA by PCR using universal-tagged primers may be determined. Universal-tagged primers may be incubated in a PCR reaction mixture containing gDNA, dNTPs, and DNA polymerase and subjected to specific thermal cycling conditions. The PCR products may further be subjected to 5'-nuclease assay. The efficiency of the amplification using universal-tagged primers may be determined by comparing the results from the 5'-nuclease assay on the PCR products with results of 5'-nuclease assay performed on a known concentration of gDNA not subjected to PCR amplification. Further efficiency may be determined by subjecting the PCR products generated from reactions containing universal-tagged primers to gel electrophoresis analysis. The presence of smearing in the gel electrophoresis analysis suggests "random priming" of the universal-tagged primers on the genomic DNA.

2. Further Amplification

In another embodiment, the present invention provides a method for further amplification of PCR products initially generated by the universal-tagged oligonucleotide primers. Such further amplification involves the use of the universal tag in the universal-tagged primer as a site that allows annealing of universal primers for the priming of further amplification cycles.

The method for further amplification involves 5'-nuclease assay analysis which includes a second PCR reaction, containing the PCR products resulting from the initial reaction and universal primers having homology to the universal region of the universal-tagged primers used in the initial PCR reaction. The yield of DNA amplified in this second round of amplification may be quantitated from the 5'-nuclease assay.

D. Applications of the Invention

Embodiments of the present invention include application of the invention to processes that rely on significant amplification of DNA.

One such process that relies on amplification of DNA is SNP genotyping which involves mapping and associating genetic variations with particular diseases and is especially beneficial to the study of the genetic basis of complex disease traits. SNP genotyping is of significant value to the treatment and diagnosis of particular diseases and further for pharmacogenetics which focus on identifying the genetic elements that underlie variations in patients with respect to drug responsiveness or toxicity.

Although a number of varying methods for SNP genotyping exist, most methods often require a quantity of gDNA from a particular individual or group of individuals that is sufficient for the genotyping. The isolated DNA sample for such genotyping is often subjected to an initial and critical DNA amplification step. Accordingly, one embodiment of the invention involves applying the universal-tagged primer method of DNA amplification to SNP genotyping. For example, DNA to be analyzed by SNP genotyping may be amplified using the universal-tagged primer method of the present invention and subsequently subjecting the amplified to SNP genotyping analysis. Other embodiments include applying the present invention to other multiplex genetic applications that involve DNA amplification.

EXAMPLES

The following examples are offered by way of illustration and not by way of limitation. The examples are provided so as to provide those of ordinary skill in the art with a complete disclosure and description of how to make and use the compounds, compositions, and methods of the invention and are not intended to limit the scope of what the inventors regard as their invention. Efforts have been made to insure accuracy with respect to numbers used (e.g. amounts, temperature, etc.) but some experimental errors and deviation should be accounted for. The disclosures of all citations in the specification are expressly incorporated herein by reference.

Example 1

Universal-Tagged Primers

The substitution of nucleic acids in a primer with nucleic acid analogues, having backbone modifications (Amberg et al., *Nucleosides Nucleotides Nucleic Acids*, 20(4–7):1275–8 (2001); Obika et al., *Bioorg Med Chem*, 9(4):1001–11 (2001); Jones et al., *Nucleic Acids Res*, 24(21):4117–22 (1996)) may affect the $T_m$ of the nucleic acid sequence. For example, locked nucleic acid (LNA) may induce an increase in the thermal stability (melting temperature (Tm)) of duplexes toward complementary DNA (Wahlestedt et al., *Proc. Natl. Acad. Sci. USA*, 97(10) 5633–5638 (2000); Petersen et al., *J Mol Recognit*, 13(1):44–53 (2000)).

The present example demonstrates the effects of the substitution of oligonucleotide primers with conformationally modified nucleic acid analogues.

A. Effect of LNA Substitution

To examine the effects of LNA substitution on DNA amplification efficiency, primers of 9 or 10 bases in length that have LNA base substitutions (Table 2) and designed to have homology with the synthetic target were incubated with a synthetic target (Table 2), containing sites for the LNA substituted primers, the 5'-nuclease probe, 5'-nuclease forward and reverse primers, dNTPs, and DNA polymerase and subjected to specific thermal cycling conditions. The yield of the PCR products resulting from the reaction were quantitated by 5'-nuclease analysis.

The template contains sites (5'-NNNNaaaaaa (SEQ ID NO: 8) and 5'-ttttttNNNN (SEQ ID NO: 9) for binding of the LNA-substituted primers. For further 5'-nuclease analysis of the PCR products generated, the template contains sites for binding of the 5'-nuclease probe, forward and reverse primers (Table 2). In the sequences in Table 2, a base in bold and upper case (e.g. T) represents a LNA base, the lower case t is the normal base, and n is a degenerate base (A or C or G or T).

TABLE 2

Sequences of synthetic template and LNA substituted primers

| Primer Name | Sequence (5'–3') |
| --- | --- |
| Template | tttttnnnncctagcgtagtgagcatccgtaagcattcatcgtga ggggtctttgtcctcctatggtagcagtcacgaggcatnnnna aaaaa (SEQ ID NO: 10) |
| 5'-nuclease Forward Primer | cctagcgtagtgagcatccgt (SEQ ID NO: 11) |
| 5'-nuclease Reverse Primer | atgcctcgtgactgctacca (SEQ ID NO: 12) |

TABLE 2-continued

Sequences of synthetic template and LNA substituted primers

| Primer Name | Sequence (5'–3') |
|---|---|
| 5'-nuclease Probe | FAM-aagcattcatcgtgaggggtctttgtcctccta (SEQ ID NO: 13)-TMR |
| LNA9T5n4 | TTTTTnnnn (SEQ ID NO: 14) |
| LNA9T6n3 | TTTTTTnnn |
| LNA10T6n4 | TTTTTTnnnn (SEQ ID NO: 15) |

The PCR mixture includes 5 µL of 100 fM of the synthetic target, 5 µL of either the 9-mer and 10 mer, having a binding region, (10 µM), 5 µL of 10× Buffer, 5 µL of 25 mM MgCl$_2$, 5 µL of 2.5 mM dNTPs, 1 µL of Taq-Gold polymerase (5U/µL), and 24 µL of distilled deionized H$_2$O (ddH$_2$O). The conditions for the PCR cycles were an initial denaturation at 95° C. for 10 minutes, followed by 30 to 40 cycles of the following: 95° C. for 30 seconds, either 55° C. or 45° C. for 3 minutes and 72° C. for 1 minute.

Following the PCR procedure, the PCR products were diluted by 100-fold prior to 5'-nuclease analysis. The yields were quantified by 5'-nuclease real-time analysis, and the results were summarized in Table 3.

TABLE 3

5'-nuclease analysis results of PCR amplification using LNA substituted primers

| Primer Used | PCR Yield @ 55° C. | PCR Yield @ 45° C. |
|---|---|---|
| LNA9T5n4 | 0.0026 nM | 0.0034 nM |
| LNA10T6n4 | 0.23 nM | 0.2 nM |
| LNA9T6n3 | 0.012 nM | 0.01 nM |
| Positive Control | 3.3 nM | 3.3 nM |
| No primer | 0.002 nM | 0.0059 nM |
| No template | 0 | 0 |

Before amplification, the initial concentration of the template was 10 fM. The annealing temperature at 55° C. and 45° C. resulted in similar yields in all cases. Here, a 10-mer primer, having a binding region, substituted with 6 LNA bases is able to amplify the synthetic target about 2.3×10$^4$-fold after 30 cycles of PCR. 9-mer primers, having a binding region, substituted with LNA bases resulted in little amplification under the PCR conditions.

B. Effect of Universal-Tagging of Primers

The substitution of LNA bases are further examined for their effect on the efficiency of amplification using short, oligonucleotide primers fused to a universal tag. LNA substituted primers may be expected to increase the Tm of the primer.

To determine whether LNA substitution of bases in universal-tagged specific primers, lacking random regions, has an effect on the efficiency of PCR amplification, real-time analysis was performed on 5'-nuclease assay PCR reactions containing a synthetic template (Table 4), having sites for the universal-tagged specific primers, the 5'-nuclease forward and reverse primer, 5'-nuclease probe and universal-tagged specific primers, specifically designed to have homology with the synthetic template and to contain base substitution with either 0, 1, 2, 3 or 5 LNA bases was performed. The efficiency of amplification was analyzed by subjecting the PCR products to gel electrophoresis analysis and 5'-nuclease analysis. Further, quantitative analysis of the copy efficiency was obtained by the 5'-nuclease analysis.

Figure 4:
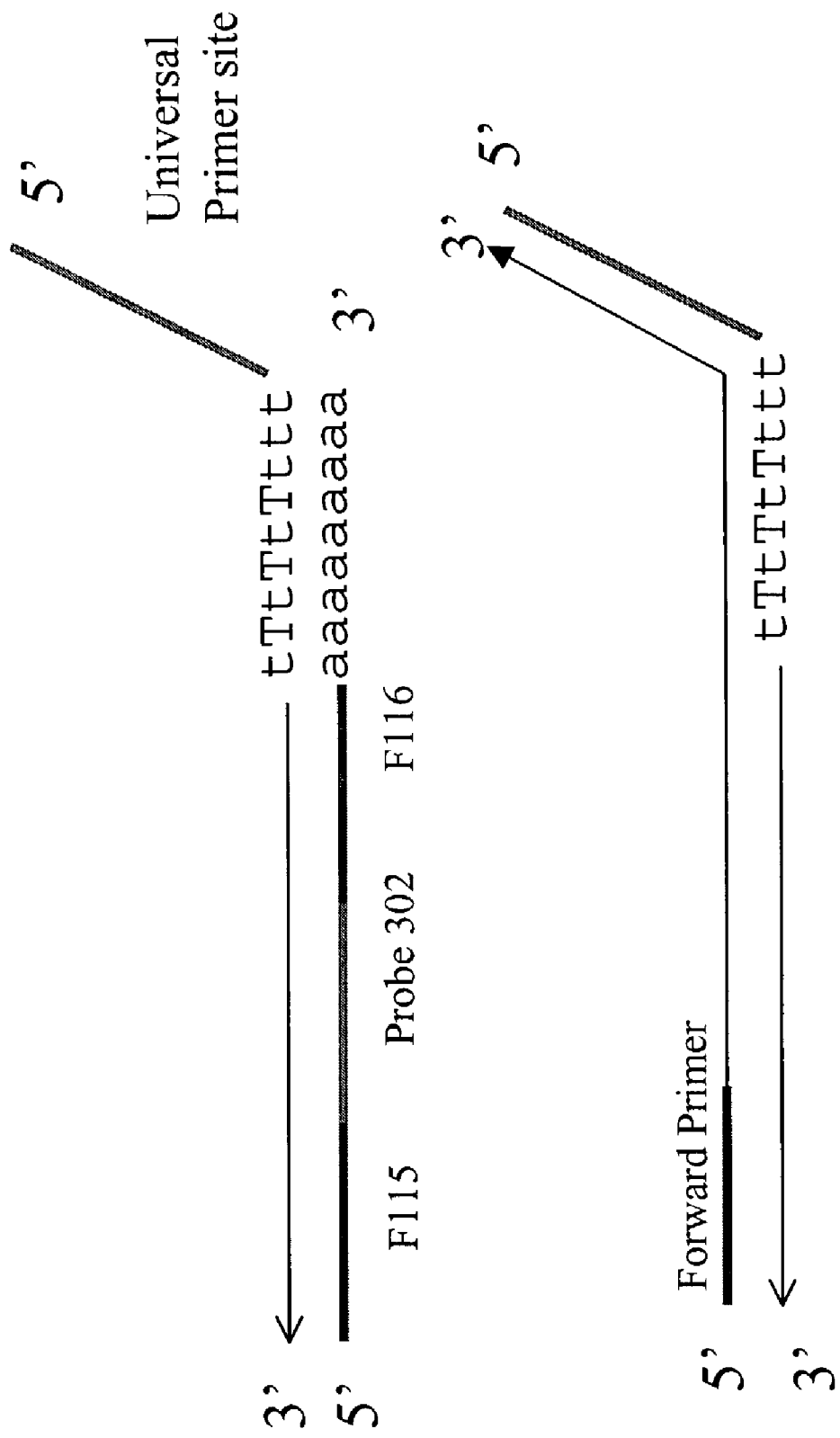
FIG. 4 is a schematic of PCR amplification using locked nucleic acid (LNA) substituted single-stranded oligonucleotide primers comprising a 3' specific region (5'-TTTtTtTtT) and a 5' universal region that may serve as a universal priming site for further PCR amplification. LNA residues are shown in capital letters, e.g. T, while normal nucleic acids are shown in lower case letters, e.g. t.

The schematic for such an experiment is depicted in FIG. 4. During the thermal cycles of the PCR reactions described below, the universal-tagged specific primer anneals to the primer site and extends to make a copy of the template. Subsequently, the forward primer extends along the copy of the template that has LNA bases and a universal tag. If the Taq DNA polymerase can copy the LNA bases efficiently, the PCR product will be extended through the LNA bases and form a longer template incorporating the universal primer site.

For such PCR reactions, the template (Table 4) contains a site (5'-aaaaaaaaaaaaaa) (SEQ ID NO: 16) for binding of the universal-tagged specific primer. Further, the template contains sites for binding of 5'-nuclease forward (5'-cctagcgtagtgagcatccgt) (SEQ ID NO: 17) and reverse (5'-tggtagcagtcacgaggcat) (SEQ ID NO: 18) primers, and a 5'-nuclease probe (5'-gaagtggcaacagagaaggaa) (SEQ ID NO: 19). The uppercase and bold letters (e.g. T) in column 2 of Table 4 represents a LNA base and the lower case t is the normal base.

TABLE 4

5'-nuclease Ct values of LNA-substituted primers

| Primer Name | Sequence (5'–3') | Notes | Ct Value |
|---|---|---|---|
| | | Positive Control | 15.7 |
| 9t-U | atgcctcgtagactgcgtacgttttttttt (SEQ ID NO: 20) | Universal-tagged 9 base specific primer, 0-LNA | 18.6 |
| 10t-U | atgcctcgtagactgcgtacgtttttttttt (SEQ ID NO: 21) | Universal-tagged 10 base specific primer, 0-LNA | 17.5 |
| 10t-1-LNA | atgcctcgtagactgcgtacgttttTttttt (SEQ ID NO: 22) | Universal-tagged 10 base specific primer, 1-LNA | 17.0 |
| 10t-2-LNA | atgcctcgtagactgcgtacgttTtTttttt (SEQ ID NO: 23) | Universal-tagged 10 base specific primer, 2-LNA | 17.7 |
| 10t-3-LNA | atgcctcgtagactgcgtacgttTtTtTttt (SEQ ID NO: 24) | Universal-tagged 10 base specific primer, 3-LNA | 25.4 |
| 10t-5-LNA | atgcctcgtagactgcgtacgtTTTTTtttt (SEQ ID NO: 25) | Universal-tagged 10 base specific primer, 5-LNA | 40 |

TABLE 4-continued

5'-nuclease Ct values of LNA-substituted primers

| Primer Name | Sequence (5'–3') | Notes | Ct Value |
|---|---|---|---|
| No template | | Negative Control | 40 |
| Template | cctagcgtagtgagcatccgtaGAAGT GGCAACAGAGAAGGAAtggt agcagtcacgaggcataaaaaaaaaaaaa (SEQ ID NO: 26) | | |

For the PCR reactions, the initial concentration of the template was 100 fM and the concentrations of the primers from Table III were 1 mM in a 25 mL reaction volume. Specifically, the 5'-nuclease PCR mixture contains 2.5 μL synthetic template (μpM), 1.25 μL 5'-nuclease probe 113 (5 μM), 2.5 μL forward 5'-nuclease primer 115 (1–10 μM), 3.75 μL ddH$_2$O, 12.5 μL 2×Master mixture for 5'-nuclease, and 2.5 μL primers selected from Table III (1.6 nM-10 μM) from Table III. The 5'-nuclease PCR mixture is subjected to an initial incubation for 2 minutes at 50° C., an incubation for 10 minutes at 95° C., and 50 cycles of the following: 15 seconds at 95° C., 1 minute at 50° C., and 1 minute at 60° C.

Upon completion of the thermal cycles, an aliquot of the PCR products was subjected to gel electrophoresis analysis.

The gel electrophoresis analysis of the PCR products showed that the control experiment with normal primers formed the 60 bp products. However, the products with forward primer and the universal tagged 9-mer or 10-mer, having a specific binding region, (referred to in Table III as 9t and 10t, respectively), were 20 bp longer. The increase in length indicated that these PCR products included a 20 base universal tag. The products of primers, 9t-U, 10t-U, 10t-1-LNA, and 10t-2-LNA had clear bands on the gel while the products of primers, 10t-3-LNA and 10t-5-LNA gave no detectable bands.

The 5'-nuclease results are summarized in Table 4. Cycle threshold (Ct) values indicate that the higher Tm provided by substitution with LNA bases did not correlate with greater efficiency in PCR amplification. For example, the primer 10t-5-LNA that has 5 LNA bases did not amplify the template. It may be that the enzymes cannot copy 5 LNA bases effectively. The primers with no LNA base substitutions, 9t-U and 10t-U, had Ct values of 18.6 and 17, respectively, and were able to significantly amplify the template with efficiency similar to amplification with normal specific primers. The primers with LNA substitutions amplified the template with similar efficiencies or worse efficiencies than efficiencies using primers without LNA substitutions. The substitution with LNA bases which increases the Tm did not significantly affect the efficiency of PCR amplification. For example, 10t-3-LNA (Ct+25.41) was significantly less efficient, although the Tm of 10t-3-LNA primer is higher than that of 10t-1-LNA, 10t-2-LNA, and 10t-U. $C_T$ represents the cycle at which amplification becomes exponential.

Example 2

Method of Using the Universal-Tagged Oligonucleotide Primers

A. Amplification of gDNA

To determine whether universal-tagged primers can amplify gDNA, amplification of human gDNA was performed using exemplary universal-tagged primers (FIG. 7), containing a 17 base universal region, a 4 base random region, and a 5 base specific region. In this particular instance, the specific region was not selected from the top 20 most frequently occurring 5-mers in the human genome (FIG. 1). The COX6b gene was selected as a test target for the gDNA amplification, based on bioinformatic e-PCR predictions. The efficiency of the amplification using a set of universal-tagged primers was compared to the efficiency calculated from amplification using different sets of primers, selected from Table IV. The schematic sequence structure of the human COX6b gene (SEQ ID NO: 35) is represented in FIG. 5 with the location of each of the primer sites clearly designated.

The oligonucleotide primers used for amplification of gDNA are described in Table 5. The universal tagged sequences were 5'-CATGGAGTGTTGGCCAGGA (U2) (SEQ ID NO: 2) and 5'-AGTGGTGCCAGCTCAGCAG (U1) (SEQ ID NO: 1). N represents one of the normal bases, A, C, G, or T.

TABLE 5

Sequences of primers used in primer sets for amplification of gDNA

| Primer Name | Sequence (5'-3') | |
|---|---|---|
| COX6b-Fa-U2 | CATGGAGTGTTGGCCAGGAGGTCACAGA | (SEQ ID NO:27) |
| COX6b-Fb-U2 | CATGGAGTGTTGGCCAGGAGGGATGAGC | (SEQ ID NO:28) |
| COX6B-Ra-U1 | AGTGGTGCCAGCTCAGCAGCCTGGGAGA | (SEQ ID NO:29) |
| U2-GGCTG | CATGGAGTGTTGGCCAGGANNNNGGCTG | (SEQ ID NO:30) |

TABLE 5-continued

Sequences of primers used in primer sets for amplification of gDNA

| Primer Name | Sequence (5'-3') | |
|---|---|---|
| U1-GGAGA | AGTGGTGCCAGCTCAGCAGNNNNGGAGA | (SEQ ID NO:31) |
| COX6-F58 | AGCAACGGGCTGAAGGC | (SEQ ID NO:32) |
| COX6-R58 | TGGAGGACAGAGGAAAGGGA | (SEQ ID NO:33) |
| COX-Probe | FAM-AGATGCAGCCAGTTCAGATCTTCCCG-TMR | (SEQ ID NO:34) |

The PCR reactions contained the following: 2 mL gDNA CEPH 1347–02 (50 ng/μL) (100 ng genomic DNA), according to the combinations outlined in Table V, 2 μL of each of the two primers (10 μM) selected from Table IV, 2 μL 10×Buffer, 2 μL MgCl$_2$ (25 mM), 2 μL dNTPs (2.5 mM), 1 μL Taq-Gold polymerase (5U/μL), 7 μL ddH$_2$O. The reactions were subjected to thermal cycling according to the following: an initial incubation for 10 minutes at 95° C., 30 cycles of 30 seconds at 95° C., 1 minute at 50° C., 1 minute at 72° C. and a final incubation for 7 minutes at 72° C., before incubation at 4° C.

The PCR products were subjected to gel electrophoresis analysis and 5'-nuclease analysis. For gel electrophoresis analysis, an aliquot of the PCR products were separated on an agarose gel by gel electrophoresis. Gel electrophoresis analysis of the PCR products from reactions containing the normal F58 and R56 specific primers showed the production of one correct main product and some longer fragments. Gel electrophoresis analysis of the PCR products from reactions containing the universal-tagged 9-mers, having a binding region, showed the production of a number of smeared bands that resulted from the "random priming" of the universal-tagged 9-mers, having a binding region, on the genomic DNA.

For 5'-nuclease analysis, the PCR products from the reactions containing various primer combinations were diluted 1000-fold. The reactions subjected to 5'-nuclease analysis were as follows: 1.25 μL 5'-nuclease or FRET probe (5 μM), 2.5 μL F58 primer (1 μM), 2.5 μL R58 primer (1 μM), 3.75 μL ddH$_2$O, 12.5 μL 2×Master mixture for 5'-nuclease, and 2.5 μL of the 1000-fold diluted PCR product. The thermal conditions for 5'-nuclease analysis were 2 minutes at 50° C., 10 minutes at 95° C., and 40 cycles of 15 seconds at 95° C. and 1 minute at 60° C.

In result (Table 6), sets of primers containing a specific 5-mer region, a 4-mer random base region, and a universal tag (FIG. 7) were able to amplify the COX6b gene from 100 ng of gDNA about 500-fold when the results from the 5'-nuclease results were compared to 5'-nuclease results performed with 100 ng gDNA.

TABLE 6

5'-nuclease Ct values using sets of primers, either universal-tagged primers or universal-tagged specific primers, as PCR primers.

| PCR Primer Sets | Ct: PCR Products 1000-fold dilution | Predicted Ct |
|---|---|---|
| F58 + R58 | 11.9 | |
| F58 + COX-Ra-U1 | 14.11 | |
| COX-Fa-U2 + R58 | 16.25 | |

TABLE 6-continued

5'-nuclease Ct values using sets of primers, either universal-tagged primers or universal-tagged specific primers, as PCR primers.

| PCR Primer Sets | Ct: PCR Products 1000-fold dilution | Predicted Ct |
|---|---|---|
| COX-Fa-U2 + COX-Ra-U1 | 18.06 | 18 |
| COX-Fb-U2 + R58 | 16.61 | |
| COX-Fb-U2 + COX-Ra-U1 | 19.72 | 18 |
| U2-GGCTG + R58 | 16.9 | |
| U2-GGCTG + COX-Ra-U1 | 16.6 | |
| F58 + U1-GGAGA | 16.8 | |
| COX-Fa-U2 + U1-GGAGA | 16.3 | 16 |
| U2-GGCTG + U1-GGAGA | 17.7 | 18 |
| 100 ng gDNA | 17.7 | |
| H$_2$O | 40 | |
| H$_2$O + COX-Ra-U1 | 40 | |

B. Further Amplification of Universal-tagged Oligonucleotide Primer-generated PCR Products Using Universal Primers PCR products generated using sets of universal-tagged specific primers, not containing a random region, were amplified using universal primers. An initial PCR reaction, containing a synthetic template (Table 7), was performed with two 9-mer primers, having a specific binding region, (5'-CCTGGAGA and 5'-GGTCACAGA; and tagged with either U1 (5'-AGTGGTGCCAGCTCAGCAG) (SEQ ID NO: 1) or U2 (CATGGAGTGTTGGCCAGGA (SEQ ID NO: 2) universal tags, respectively, to generate COX-Ra-U1 and COX-Fa-U2, respectively (Table 6). The PCR products were diluted 1000-fold and subjected to 5'-nuclease analysis using universal primers, U1 and U2.

TABLE 7

Sequences of universal-tagged specific primers and universal primers

| Name | Sequence (5'-3') | |
|---|---|---|
| Template | GGTCACAGAcgggaagatctgaactggctgcatctttTCTCCCAGG | (SEQ ID NO:36) |
| COX-Ra-U1 | AGTGGTGCCAGCTCAGCAGCCTGGGAGA | (SEQ ID NO:29) |
| COX-Fa-U2 | CATGGAGTGTTGGCCAGGAGGTCACAGA | (SEQ ID NO:27) |
| Universal U1 Primer | AGTGGTGCCAGCTCAGCAG | (SEQ ID NO:1) |
| Universal U2 Primer | CATGGAGTGTTGGCCAGGA | (SEQ ID NO:2) |
| Taq-probe | Fam-AGATGCAGCCAGTTCAGATCTTCCCG-TMR | (SEQ ID NO:34) |

For the initial PCR reaction, 2 µL of 1 pM template and 2 µL of each of the 10 µM universal-tagged specific primers, COX-Ra-U1 and COX-Fa-U2, were incubated with 2 µL of 10×buffer, 2 µL of 25 mM MgCl$_2$, 2 µL of 2.5 mM dNTP, 1 µL of 5U/µL Taq-Gold polymerase. The thermal profile for the PCR reaction was an initial incubation for 10 minutes at 95° C., followed by 30 cycles of 30 seconds at 95° C., 1 minute at 50° C., and 1 minute at 72° C., a final cycle of 7 minutes at 72° C., and the reaction was stopped at 4° C.

The PCR products were diluted 1000-fold and subjected to 5'-nuclease analysis using the U1 and U2 universal primers described in Table 7. The reaction mixture subjected to 5'-nuclease analysis consisted of the following: 1.25 µL of 5 µM 5'-nuclease probe (Table 6), 2.5 µL of 1 µM universal U1 primer, 2.5 µL of 1 µM universal U2 primer, 3.75 µL ddH20, 12.5 µL 2×Master mix containing enzyme and buffer, 25 µL of the 1000-fold diluted PCR product that resulted from the COX-Fa-U2 and COX-Ra-U1 primed reaction described above. The thermal conditions for the 5'-nuclease assay was a 2 minute incubation at 50° C., followed by a 10 minute incubation at 95° C., followed by 50 cycles of 15 seconds at 95° C. and 1 minute at 60° C.

The results of the 5'-nuclease analysis are summarized in Table 8. The products generated using the universal-tagged specific primers, COX-Ra-U1 and COX-Fa-U2, were amplifiable using the universal U1 and U2 primers

TABLE 8

5'-nuclease assay Ct values from the second-round PCR reactions performed with universal primers

| PCR primer pairs in Initial PCR Reaction | Ct values | Template |
|---|---|---|
| COX-Ra-U1 and COX-Fa-U2 | 16.7 | PCR products of template, 1000-fold dilution |
| COX-Ra-U1 and COX-Fa-U2 | 50 | No template (control) |

All references cited throughout the specification are hereby expressly incorporated by reference. It is understood that the application of the teachings of the present invention to a specific problem or situation will be within the capabilities of one having ordinary skill in the art in light of the teachings contained herein. Examples of the products and processes of the present invention should not be construed to limit the invention.

What is claimed is:

1. A method for amplifying target DNA by polymerase chain reaction (PCR) comprising:
   providing a length of a PCR amplified product that is primed at a single specified site on a target DNA;
   preparing a mixture, of (1) said target DNA, comprising multiple DNA sequences, (2) a set of oligonucleotide primers, each primer comprising (i) a 3' specific region, wherein a sequence of said 3' specific region is selected to hybridize to the specified site on the target DNA, and wherein said specified site on the target DNA is chosen according to the length of the PCR amplified product that is primed at the specified site on the target DNA, (ii) a random region, and (iii) a 5' universal region, wherein said universal region is selected to meet a requirement of a PCR primer and serves as a first universal priming site (U1) for further PCR amplification with a complementary primer, wherein the 5' universal region, serves as an entire first universal priming site independently of the random region and the 3' specific region, (3) a DNA polymerase, and (4) multiple deoxynucleoside triphosphates (dNTPs) under conditions such that said PCR primers anneal to target DNA; and
   performing a polymerase chain reaction (PCR) to amplify the target DNA sequences in said target DNA, whereby a PCR amplified product is formed incorporating said first universal priming site (U1).

2. The method of claim 1 wherein said target DNA is genomic DNA (gDNA).

3. The method of claim 1 wherein said target DNA is complementary DNA (cDNA).

4. The method of claim 2 wherein said gDNA is human.

5. The method of claim 4 wherein at least a fraction of the whole human genome is amplified from said gDNA.

6. The method of claim 5 wherein said 3' specific region is designed to bind to a genomic sequence occurring in the human genome with a frequency of between about 0.01% and 2.0%.

7. The method of claim 1 wherein said (i) 3' specific region is between about 4 and 12 bases in length.

8. The method of claim 7 wherein said 3' specific region is 5 bases in length, and wherein an average length of the products from the PCR reaction is between 74 and 523 bases.

9. The method of claim 8 wherein the sequence of said 3' specific region is selected from the group consisting of: AAAAA; AAAAT; AAATA; TAAAA; AGAAA; ATAAA; AAATT; TTAAA; GAAAA; AATAA; CAAAA; AAGAA;

AAAGA; AAAAG; AAATG; AAACA; ACAAA; ATTTA; TGAAA; ATATA; AATAT; AAAAC; AGAGA; AATTA; AATTA; AGGAA; AACAA; CCCAG; TCAAA; ATTTC; ATAAT; ACACA; CAGAA; AGAAT; GAGAA; GGAAA; TCCCA; ATTAA; ATGAA; AAAGT; AATGA; TTCAA; ATTTG; TCTCA; ACAGA; AAACT; CCAGG; AGAAG; and TATAA.

10. The method of claim 1 wherein said (ii) random region is between about 2 and 15 bases in length.

11. The method of claim 10 wherein said random region is 4 bases in length.

12. The, method of claim 11 wherein the random regions present in said primers include all 256 possible combinations of adenosine, cytosine, guanine, and thymidine.

13. The method of claim 1 wherein said (iii) 5' universal region is between about 12 and 35 bases in length.

14. The method of claim 13 wherein the sequence of the 5' universal region is selected from the group consisting of:
AGTGGTGCCAGCTCAGCAG (SEQ ID NO: 1);
CATGGAGTGTTGGCCAGGA (SEQ ID NO: 2);
AACTCTCTCCCAAGAGCGA (SEQ ID NO: 3);
TAGCGTAGTGAGCATCCGT (SEQ ID NO: 4);
TCCCACATTCACCGCTTAG (SEQ ID NO: 5);
TGTAAAACGACGGCCAGT (SEQ ID NO: 6); and
GTACGCAGTCTACGAGGC (SEQ ID NO: 7).

15. The method of claim 4 wherein said 5' universal region is designed to have at least 2 mismatches as compared to any segment of the same length in the human genome.

16. The method of claim 1 further comprising the step of extending said copy to encode a second universal priming site (U2).

17. The method of claim 16 comprising the step of further amplifying said amplified product with two primers complementing said first and second universal priming sites (U1 and U2).

18. The method of claim 1 wherein said DNA polymerase is a Taq DNA polymerase.

19. The method of claim 18 wherein said DNA polymerase is selected from the group consisting of a DNA polymerase which is chemically modified to allow for a hot start, a DNA polymerase which is recombinantly produced and modified to remove exonuclease activity, and the Stoffel fragment of a natural or recombinant DNA polymerase.

20. The method of claim 17 further comprising the step of single-nucleotide polymorphism (SNP) genotyping.

21. The method of claim 1 wherein the set of oligonucleotide primers used is provided according to bioinformatic prediction of expected products using in silico e-PCR.

22. The method of claim 1 or claim 17 further comprising the step of detecting the amplified product by subjecting the product to a 5'-nuclease assay.

23. The method of claim 22 wherein the detection comprises:
annealing a fluorogenic oligonucleotide probe to the amplified DNA;
cleaving the probe by the 5'-nuclease activity of the DNA polymerase; and
quantitating a change in fluorescence.

24. An oligonucleotide primer for polymerase chain reaction (PCR), comprising (1) a distinct 3' specific region of between about 4 and 12 bases in length, wherein said 3' specific region hybridizes to a single specified site on a target, wherein the specified site is configured so that a PCR product initiated at the specified site on the target by the 3' specific region will result in products with an average length of between 74 and 523 bases, (2) a distinct random region of between about 2 and 15 bases in length, and (3) a distinct 5' universal region of about 12 and 35 bases in length, wherein the universal region does not bind to an initial target DNA when the 3' specific region binds to the initial target DNA, wherein the random region is located between the 3' specific region and the 5' universal region, and wherein the 5' universal region hybridizes to a second primer so as to allow priming at the 5' universal region.

25. The primer of claim 24 wherein said 3' specific region is 5 bases in length.

26. The primer of claim 25 wherein the sequence of said 3' specific region is selected from the group consisting of:
AAAAA; AAAAT; AAATA; TAAAA; AGAAA; ATAAA; AAATT; TTAAA; GAAAA; AATAA; CAAAA; AAGAA; AAAGA; AAAAG; AAATG; AAACA; ACAAA; ATTTA; TGAAA; ATATA; AATAT; AAAAC; AGAGA; AATTA; AATTA; AGGAA; AACAA; CCCAG; TCAAA; ATTTC; ATAAT; ACACA; CAGAA; AGAAT; GAGAA; GGAAA; TCCCA; ATTAA; ATGAA; AAAGT; AATGA; TTCAA; ATTTG; TCTCA; ACAGA; AAACT; CCAGG; AGAAG; and TATAA.

27. The primer of claim 24 wherein the 3' specific region is designed to bind a genomic sequence occurring in the human genome with a frequency of between about 0.01% and 2.0%.

28. The primer of claim 24 wherein said random region is 4 bases in length.

29. The primer of claim 28 wherein the sequence of said random region is selected from the group consisting of the $4^4$ possible combinations of bases.

30. The primer of claim 24 wherein said universal region is designed to have no significant homology to any segment in the human genome.

31. A set of oligonucleotide primers for amplification of genomic DNA (gDNA) in a polymerase chain reaction (PCR), each of said primers comprising (1) a distinct 3' specific region of between about 4 and 12 bases in length, wherein said 3' specific region hybridizes to a specified site on a target, and wherein said specified site is a nucleic acid sequence that occurs at a frequency in the target so that a PCR product, from priming at the 3' specific region, will allow for partial amplification of a whole target by the PCR product, (2) a distinct random region of between about 2 and 15 bases in length, and (3) a distinct 5' universal region of between about 12 and 35 bases in length, wherein the universal region is selected so that it meets a requirement of a PCR primer, wherein the 5' universal region, serves as an entire first universal priming site independently of the random region and the 3' specific region, wherein the random region is located between the 3' specific region and the 5' universal region, and wherein said 5' universal region hybridizes to a second primer so as to allow priming at the 5' universal region.

32. The set of claim 31 wherein in each primer the 3' specific region is 5 bases in length.

33. The set of claim 32 wherein the sequence of the 3' specific region is selected from the group consisting of:
AAAAA; AAAAT; AAATA; TAAAA; AGAAA; ATAAA; AAATT; TTAAA; GAAAA; AATAA; CAAAA; AAGAA; AAAGA; AAAAG; AAATG; AAACA; ACAAA; ATTTA; TGAAA; ATATA; AATAT; AAAAC; AGAGA; AATTA; AATTA; AGGAA; AACAA; CCCAG; TCAAA; ATTTC; ATAAT; ACACA; CAGAA; AGAAT; GAGAA; GGAAA; TCCCA; ATTAA; ATGAA; AAAGT; AATGA; TTCAA; ATTTG; TCTCA; ACAGA; AAACT; CCAGG; AGAAG; and TATAA.

34. The set of claim 31 wherein in each primer the random region is 4 bases in length.

35. The set of claim 34 wherein the random regions present in said primers include all 4⁴ possible combinations of adenosine, cytosine, guanine and thymidine.

36. The set of claim 31 wherein the sequence of the 5' universal region is selected from the group consisting of:
AGTGGTGCCAGCTCAGCAG (SEQ ID NO: 1);
CATGGAGTGTTGGCCAGGA (SEQ ID NO: 2);
AACTCTCTCCCAAGAGCGA (SEQ ID NO: 3)
TAGCGTAGTGAGCATCCGT (SEQ ID NO: 4);
TCCCACATTCACCGCTTAG (SEQ ID NO: 5);
TGTAAAACGACGGCCAGT (SEQ ID NO: 6); and
GTACGCAGTCTACGAGGC (SEQ ID NO: 7).

37. A primer-target duplex comprising the oligonucleotide primer of claim 24 and a target DNA wherein the binding region of the oligonucleotide primer is annealed to the target DNA.

38. The method of claim 1, wherein a first polymerase chain reaction occurs in the absence of a complementary primer to the 5' universal region; and wherein a second polymerase chain reaction is performed, wherein the second polymerase chain reaction employs a complementary primer to the 5' universal region, wherein said complementary primer binds to the 5' universal region.

39. A method for amplifying target DNA by polymerase chain reaction (PCR) comprising:
providing a length of a PCR product that is primed at a single specified site on a target DNA;
preparing a mixture, of (1) said target DNA, comprising multiple DNA sequences, (2) a set of oligonucleotide primers, each primer comprising (i) a 3' specific region, wherein said 3' specific region hybridizes to the specified site on the target DNA, wherein said specified site is selected based on a frequency of the specified site in the target DNA that allows for partial amplification of an entire genome, (ii) a random region, and (iii) a 5' universal region, wherein said universal region serves as a first universal priming site (U1) for further PCR amplification with a complementary primer, and wherein said universal region is selected to meet a requirement of a PCR primer, wherein the 5' universal region, serves as an entire first universal priming site independently of the random region and the 3' specific region, (3) a DNA polymerase, and (4) multiple deoxynucleoside triphosphates (dNTPs) under conditions such that said PCR primers anneal to target DNA;
performing a polymerase chain reaction (PCR) to amplify the target DNA sequences in said target DNA, whereby an amplified product is formed incorporating said first universal priming site (U1); and
adding a complementary primer that is configured to hybridize to the 5' universal region, and performing a further polymerase chain reaction to amplify the sequences primed from the universal priming site.

40. The method of claim 8 wherein the sequence of said 3' specific region comprises a sequence selected from the group consisting of: AAAAA; AAAAT; AAATA; TAAAA; AGAAA; ATAAA; AAATT; TTAAA; GAAAA; AATAA; CAAAA; AAGAA; AAAGA; AAAAG; AAATG; AAACA; ACAAA; ATTTA; TGAAA; ATATA; AATAT; AAAAC; AGAGA; AATTA; AATTA; AGGAA; AACAA; CCCAG; TCAAA; ATTTC; ATAAT; ACACA; CAGAA; AGAAT; GAGAA; GGAAA; TCCCA; ATTAA; ATGAA; AAAGT; AATGA; TTCAA; ATTTG; TCTCA; ACAGA; AAACT; CCAGG; AGAAG; and TATAA.

41. The method of claim 13 wherein the sequence of the 5' universal region comprises a sequence selected from the group consisting of:
AGTGGTGCCAGCTCAGCAG (SEQ ID NO: 1);
CATGGAGTGTTGGCCAGGA (SEQ ID NO: 2);
AACTCTCTCCCAAGAGCGA (SEQ ID NO: 3);
TAGCGTAGTGAGCATCCGT (SEQ ID NO: 4);
TCCCACATTCACCGCTTAG (SEQ ID NO: 5);
TGTAAAACGACGGCCAGT (SEQ ID NO: 6); and
GTACGCAGTCTACGAGGC (SEQ ID NO: 7).

42. The primer of claim 25 wherein the sequence of said 3' specific region comprises a sequence selected from the group consisting of: AAAAA; AAAAT; AAATA; TAAAA; AGAAA; ATAAA; AAATT; TTAAA; GAAAA; AATAA; CAAAA; AAGAA; AAAGA; AAAAG; AAATG; AAACA; ACAAA; ATTTA; TGAAA; ATATA; AATAT; AAAAC; AGAGA; AATTA; AATTA; AGGAA; AACAA; CCCAG; TCAAA; ATTTC; ATAAT; ACACA; CAGAA; AGAAT; GAGAA; GGAAA; TCCCA; ATTAA; ATGAA; AAAGT; AATGA; TTCAA; ATTTG; TCTCA; ACAGA; AAACT; CCAGG; AGAAG; and TATAA.

43. The set of claim 32 wherein the sequence of the 3' specific region comprises a sequence selected from the group consisting of: AAAAA; AAAAT; AAATA; TAAAA; AGAAA; ATAAA; AAATT; TTAAA; GAAAA; AATAA; CAAAA; AAGAA; AAAGA; AAAAG; AAATG; AAACA; ACAAA; ATTTA; TGAAA; ATATA; AATAT; AAAAC; AGAGA; AATTA; AATTA; AGGAA; AACAA; CCCAG; TCAAA; ATTTC; ATAAT; ACACA; CAGAA; AGAAT; GAGAA; GGAAA; TCCCA; ATTAA; ATGAA; AAAGT; AATGA; TTCAA; ATTTG; TCTCA; ACAGA; AAACT; CCAGG; AGAAG; and TATAA.

44. The set of claim 31 wherein the sequence of the 5' universal region comprises a sequence selected from the group consisting of:
AGTGGTGCCAGCTCAGCAG (SEQ ID NO: 1);
CATGGAGTGTTGGCCAGGA (SEQ ID NO: 2);
AACTCTCTCCCAAGAGCGA (SEQ ID NO: 3)
TAGCGTAGTGAGCATCCGT (SEQ ID NO: 4);
TCCCACATTCACCGCTTAG (SEQ ID NO: 5);
TGTAAAACGACGGCCAGT (SEQ ID NO: 6); and
GTACGCAGTCTACGAGGC (SEQ ID NO: 7).

45. An oligonucleotide primer and target for polymerase chain reaction (PCR), the primer comprising:
(1) a distinct 3' specific region of between about 4 and 12 bases in length, wherein said 3' specific region hybridizes to a single specified site on a target, wherein said specified site is a nucleic acid sequence that occurs in the target at positions so that a PCR reaction using the 3' specific region as a primer to the specified site will result in PCR products with an average length of 74–523 base pairs, (2) a distinct random region of between about 2 and 15 bases in length, and (3) a distinct 5' universal region of about 12 and 35 bases in length, wherein the 5' universal region serves as a priming site for a primer, wherein the random region is located between the 3' specific region and the 5' universal region; and
the target comprising a specified site, wherein said specified site is a region with significant homology to the 3' specific region of the primer to which the 3' specific region of the primer may attach.

46. A combination of two primers for a polymerase chain reaction (PCR) comprising:
a first primer comprising (1) a distinct 3' specific region of between about 4 and 12 bases in length, wherein said 3' specific region hybridizes to a specified site in a DNA sequence, wherein said single specified site is a nucleic acid sequence that occurs in the DNA sequence such that a distance between specified sites is such that the entire target can be sequenced through PCR at multiple specified sites (2) a distinct random region of between about 2 and 15 bases in length, and (3) a distinct 5' universal region of about 12 and 35 bases in length, wherein the 5'universal region is configured to bind to a second primer, and wherein said 5' universal region is configured to meet a requirement of a PCR primer, wherein the 5' universal region, serves as an entire first universal priming site independently of the random region and the 3' specific region, wherein the random region is located between the 3' specific region and the 5' universal region; and a second primer configured to hybridize to the 5' universal region.

* * * * *

UNITED STATES PATENT AND TRADEMARK OFFICE
CERTIFICATE OF CORRECTION

PATENT NO.       : 7,176,002 B2
APPLICATION NO.  : 10/151061
DATED            : February 13, 2007
INVENTOR(S)      : Kai Qin Lao et al.

It is certified that error appears in the above-identified patent and that said Letters Patent is hereby corrected as shown below:

On the Title page, item 56 Col. 2 (Other Publications), lines 4-5, please delete "Thermus Aquaticus" and insert --THERMUS AQUATICUS--, therefor.

On the Title page, item 56 Col. 2 (Other Publications), line 15, after "oligonucleotide" please insert --primed--.

Col. 8, line 11, please delete "dye 's" and insert --dye's--, therefor.

Col. 9, lines 21-23 (approx.), please delete ""Genomic DMA" or "gDMA" refers to all the DMA sequences comprising the entire genome of an organism." and insert ""Genomic DNA" or "gDNA" refers to all the DNA sequences comprising the entire genome of an organism." in a new paragraph following the deleted section.

Col. 12, line 62, please delete "G. D.," and insert --G.D.,-- therefor.

Col. 14, line 25 (approx.), please delete "Chem ," and insert --Chem,--, therefor.

Col. 17, line 18 (approx.), please delete "(μpM)," and insert --(1pM),--, therefor.

Col. 22, line 20 (approx.), after "primers" please insert -- . --.

Col. 37, line 12, Claim 12, please delete "The," and insert -- The--, therefor.

Col. 40, line 64, Claim 46, after "hybridizes to a" please insert --single--.

Col. 40, line 65, Claim 46, after "wherein said" please delete "single".

Col. 41, line 5, Claim 46, please delete "5 'universal" and insert --5' universal--, therefor.

Signed and Sealed this

Twenty-eighth Day of August, 2007

JON W. DUDAS
*Director of the United States Patent and Trademark Office*

SEQUENCE LISTING

<160> NUMBER OF SEQ ID NOS: 36

<210> SEQ ID NO 1
<211> LENGTH: 19
<212> TYPE: DNA
<213> ORGANISM: Artificial Sequence
<220> FEATURE:
<223> OTHER INFORMATION: Synthetic oligonucleotide primer designed to
      have no significant homology to the human genome.

<400> SEQUENCE: 1
agtggtgcca gctcagcag                                                19

<210> SEQ ID NO 2
<211> LENGTH: 19
<212> TYPE: DNA
<213> ORGANISM: Artificial Sequence
<220> FEATURE:
<223> OTHER INFORMATION: Synthetic oligonucleotide primer designed to
      have no significant homology to the human genome.

```
<400> SEQUENCE: 2
catggagtgt tggccagga                                              19

<210> SEQ ID NO 3
<211> LENGTH: 19
<212> TYPE: DNA
<213> ORGANISM: Artificial Sequence
<220> FEATURE:
<223> OTHER INFORMATION: Synthetic oligonucleotide primer designed to
      have no significant homology to the human genome.

<400> SEQUENCE: 3
aactctctcc caagagcga                                              19

<210> SEQ ID NO 4
<211> LENGTH: 19
<212> TYPE: DNA
<213> ORGANISM: Artificial Sequence
<220> FEATURE:
<223> OTHER INFORMATION: Synthetic oligonucleotide primer designed to
      have no significant homology to the human genome.

<400> SEQUENCE: 4
tagcgtagtg agcatccgt                                              19

<210> SEQ ID NO 5
<211> LENGTH: 19
<212> TYPE: DNA
<213> ORGANISM: Artificial Sequence
<220> FEATURE:
<223> OTHER INFORMATION: Synthetic oligonucleotide primer designed to
      have no significant homology to the human genome.

<400> SEQUENCE: 5
tcccacattc accgcttag                                              19

<210> SEQ ID NO 6
<211> LENGTH: 18
<212> TYPE: DNA
<213> ORGANISM: Artificial Sequence
<220> FEATURE:
<223> OTHER INFORMATION: Synthetic oligonucleotide primer designed to
      have no significant homology to the human genome.

<400> SEQUENCE: 6
tgtaaaacga cggccagt                                               18

<210> SEQ ID NO 7
<211> LENGTH: 18
<212> TYPE: DNA
<213> ORGANISM: Artificial Sequence
<220> FEATURE:
<223> OTHER INFORMATION: Synthetic oligonucleotide primer designed to
      have no significant homology to the human genome.

<400> SEQUENCE: 7
gtacgcagtc tacgaggc                                               18

<210> SEQ ID NO 8
<211> LENGTH: 10
<212> TYPE: DNA
<213> ORGANISM: Artificial Sequence
<220> FEATURE:
<223> OTHER INFORMATION: Synthetic oligonucleotide template having no
      significant homology to the human genome.
<220> FEATURE:
```

<221> NAME/KEY: unsure
<222> LOCATION: 1, 2, 3, 4
<223> OTHER INFORMATION: n = A, T, C or G

<400> SEQUENCE: 8 nnnnaaaaaa                                                            10

<210> SEQ ID NO 9
<211> LENGTH: 10
<212> TYPE: DNA
<213> ORGANISM: Artificial Sequence
<220> FEATURE:
<223> OTHER INFORMATION: Synthetic oligonucleotide template having no
      significant homology to the human genome.
<220> FEATURE:
<221> NAME/KEY: unsure
<222> LOCATION: 7, 8, 9, 10
<223> OTHER INFORMATION: n = A, T, C or G

<400> SEQUENCE: 9 tttttttnnnn                                                           10

<210> SEQ ID NO 10
<211> LENGTH: 93
<212> TYPE: DNA
<213> ORGANISM: Artificial Sequence
<220> FEATURE:
<223> OTHER INFORMATION: Synthetic oligonucleotide template having no
      significant homology to the human genome.
<220> FEATURE:
<221> NAME/KEY: unsure
<222> LOCATION: (0)...(0)
<223> OTHER INFORMATION: n = A, T, C or G

<400> SEQUENCE: 10
tttttnnnnc ctagcgtagt gagcatccgt aagcattcat cgtgaggggt ctttgtcctc     60
ctatggtagc agtcacgagg catnnnnaaa aaa                                  93

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide primer with homology
      to a synthetic template having no significant homology to the
      human genome.

<400> SEQUENCE: 11
cctagcgtag tgagcatccg t                                               21

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide primer with homology
      to a synthetic template having no significant homology to the
      human genome.

<400> SEQUENCE: 12
atgcctcgtg actgctacca                                                 20

<210> SEQ ID NO 13
<211> LENGTH: 33
<212> TYPE: DNA
<213> ORGANISM: Artificial Sequence
<220> FEATURE:
<223> OTHER INFORMATION: Synthetic oligonucleotide probe with  homology to a synthetic template having no significant homology to the
human genome.

<400> SEQUENCE: 13
aagcattcat cgtgagggt ctttgtcctc cta                33

<210> SEQ ID NO 14
<211> LENGTH: 9
<212> TYPE: DNA
<213> ORGANISM: Artificial Sequence
<220> FEATURE:
<223> OTHER INFORMATION: Synthetic oligonucleotide primer having no
      significant homology to the human genome.
<220> FEATURE:
<221> NAME/KEY: unsure
<222> LOCATION: 6, 7, 8, 9
<223> OTHER INFORMATION: n = A, T, C or G
<220> FEATURE:
<221> NAME/KEY: misc_feature
<222> LOCATION: 1, 2, 3, 4, 5
<223> OTHER INFORMATION: A locked nucleic acid.

<400> SEQUENCE: 14 tttttnnnn                9

<210> SEQ ID NO 15
<211> LENGTH: 10
<212> TYPE: DNA
<213> ORGANISM: Artificial Sequence
<220> FEATURE:
<223> OTHER INFORMATION: Synthetic oligonucleotide primer having no
      significant homology to the human genome.
<220> FEATURE:
<221> NAME/KEY: unsure
<222> LOCATION: (0)...(0)
<223> OTHER INFORMATION: n = A, T, C or G
<220> FEATURE:
<221> NAME/KEY: misc_feature
<222> LOCATION: 1, 2, 3, 4, 5, 6
<223> OTHER INFORMATION: A locked nucleic acid.

<400> SEQUENCE: 15 tttttttnnnn                10

<210> SEQ ID NO 16
<211> LENGTH: 14
<212> TYPE: DNA
<213> ORGANISM: Artificial Sequence
<220> FEATURE:
<223> OTHER INFORMATION: A site in a synthetic oligonucleotide template
      having no significant homology to the human genome.

<400> SEQUENCE: 16
aaaaaaaaaa aaaa                14

<210> SEQ ID NO 17
<211> LENGTH: 21
<212> TYPE: DNA
<213> ORGANISM: Artificial Sequence
<220> FEATURE:
<223> OTHER INFORMATION: A synthetic oligonucleotide primer having
      homology with a synthetic oligonucleotide template having no
      significant homology to the human genome.

<400> SEQUENCE: 17
cctagcgtag tgagcatccg t                21

<210> SEQ ID NO 18
<211> LENGTH: 20

```
<212> TYPE: DNA
<213> ORGANISM: Artificial Sequence
<220> FEATURE:
<223> OTHER INFORMATION: A synthetic oligonucleotide primer having
      homology with a synthetic oligonucleotide template having no
      significant homology to the human genome.

<400> SEQUENCE: 18
tggtagcagt cacgaggcat                                               20

<210> SEQ ID NO 19
<211> LENGTH: 21
<212> TYPE: DNA
<213> ORGANISM: Artificial Sequence
<220> FEATURE:
<223> OTHER INFORMATION: A synthetic oligonucleotide probe having
      homology with a synthetic oligonucleotide template having no
      significant homology to the human genome.

<400> SEQUENCE: 19
gaagtggcaa cagagaagga a                                             21

<210> SEQ ID NO 20
<211> LENGTH: 30
<212> TYPE: DNA
<213> ORGANISM: Artificial Sequence
<220> FEATURE:
<223> OTHER INFORMATION: A synthetic oligonucleotide primer having no
      significant homology to the human genome.

<400> SEQUENCE: 20
atgcctcgta gactgcgtac gttttttttt                                    30

<210> SEQ ID NO 21
<211> LENGTH: 31
<212> TYPE: DNA
<213> ORGANISM: Artificial Sequence
<220> FEATURE:
<223> OTHER INFORMATION: A synthetic oligonucleotide primer having no
      significant homology to the human genome.

<400> SEQUENCE: 21
atgcctcgta gactgcgtac gttttttttt t                                  31

<210> SEQ ID NO 22
<211> LENGTH: 31
<212> TYPE: DNA
<213> ORGANISM: Artificial Sequence
<220> FEATURE:
<223> OTHER INFORMATION: A synthetic oligonucleotide primer having no
      significant homology to the human genome.
<220> FEATURE:
<221> NAME/KEY: misc_feature
<222> LOCATION: 26
<223> OTHER INFORMATION: A locked nucleic acid.

<400> SEQUENCE: 22
atgcctcgta gactgcgtac gttttttttt t                                  31

<210> SEQ ID NO 23
<211> LENGTH: 31
<212> TYPE: DNA
<213> ORGANISM: Artificial Sequence
<220> FEATURE:
<223> OTHER INFORMATION: A synthetic oligonucleotide primer having no
      significant homology to the human genome.
<220> FEATURE:
<221> NAME/KEY: misc_feature
<222> LOCATION: 24, 26
```

<223> OTHER INFORMATION: A locked nucleic acid derivative.

<400> SEQUENCE: 23
atgcctcgta gactgcgtac gttttttttt t                          31

<210> SEQ ID NO 24
<211> LENGTH: 31
<212> TYPE: DNA
<213> ORGANISM: Artificial Sequence
<220> FEATURE:
<223> OTHER INFORMATION: A synthetic oligonucleotide primer having no
      significant homology to the human genome.
<220> FEATURE:
<221> NAME/KEY: misc_feature
<222> LOCATION: 24, 26, 28
<223> OTHER INFORMATION: A locked nucleic acid derivative.

<400> SEQUENCE: 24
atgcctcgta gactgcgtac gttttttttt t                          31

<210> SEQ ID NO 25
<211> LENGTH: 31
<212> TYPE: DNA
<213> ORGANISM: Artificial Sequence
<220> FEATURE:
<223> OTHER INFORMATION: A synthetic oligonucleotide primer having no
      significant homology to the human genome.
<220> FEATURE:
<221> NAME/KEY: misc_feature
<222> LOCATION: 23, 24, 25, 26, 27
<223> OTHER INFORMATION: A locked nucleic acid derivative.

<400> SEQUENCE: 25
atgcctcgta gactgcgtac gttttttttt t                          31

<210> SEQ ID NO 26
<211> LENGTH: 77
<212> TYPE: DNA
<213> ORGANISM: Artificial Sequence
<220> FEATURE:
<223> OTHER INFORMATION: A synthetic oligonucleotide template having no
      significant homology to the human genome.

<400> SEQUENCE: 26
cctagcgtag tgagcatccg tagaagtggc aacagagaag gaatggtagc agtcacgagg    60
cataaaaaaa aaaaaaa                                                  77

<210> SEQ ID NO 27
<211> LENGTH: 28
<212> TYPE: DNA
<213> ORGANISM: Artificial Sequence
<220> FEATURE:
<223> OTHER INFORMATION: A synthetic oligonucleotide primer comprising
      human sequence.

<400> SEQUENCE: 27
catggagtgt tggccaggag gtcacaga                              28

<210> SEQ ID NO 28
<211> LENGTH: 28
<212> TYPE: DNA
<213> ORGANISM: Artificial Sequence
<220> FEATURE:
<223> OTHER INFORMATION: A synthetic oligonucleotide primer comprising
      human sequence.

<400> SEQUENCE: 28

```
catggagtgt tggccaggag ggatgagc                                    28
```

<210> SEQ ID NO 29
<211> LENGTH: 28
<212> TYPE: DNA
<213> ORGANISM: Artificial Sequence
<220> FEATURE:
<223> OTHER INFORMATION: A synthetic oligonucleotide primer comprising
      human sequence.

<400> SEQUENCE: 29

```
agtggtgcca gctcagcagc ctgggaga                                    28
```

<210> SEQ ID NO 30
<211> LENGTH: 28
<212> TYPE: DNA
<213> ORGANISM: Artificial Sequence
<220> FEATURE:
<223> OTHER INFORMATION: A synthetic oligonucleotide primer having no
      significant homology to the human genome.
<220> FEATURE:
<221> NAME/KEY: unsure
<222> LOCATION: (0)...(0)
<223> OTHER INFORMATION: n = A, T, C or G

<400> SEQUENCE: 30

```
catggagtgt tggccaggan nnnggctg                                    28
```

<210> SEQ ID NO 31
<211> LENGTH: 28
<212> TYPE: DNA
<213> ORGANISM: Artificial Sequence
<220> FEATURE:
<223> OTHER INFORMATION: A synthetic oligonucleotide primer having no
      significant homology to the human genome.
<220> FEATURE:
<221> NAME/KEY: unsure
<222> LOCATION: (0)...(0)
<223> OTHER INFORMATION: n = A, T, C or G

<400> SEQUENCE: 31

```
agtggtgcca gctcagcagn nnnggaga                                    28
```

<210> SEQ ID NO 32
<211> LENGTH: 17
<212> TYPE: DNA
<213> ORGANISM: Artificial Sequence
<220> FEATURE:
<223> OTHER INFORMATION: A synthetic oligonucleotide primer comprising
      human sequence.

<400> SEQUENCE: 32

```
agcaacgggc tgaaggc                                                17
```

<210> SEQ ID NO 33
<211> LENGTH: 20
<212> TYPE: DNA
<213> ORGANISM: Artificial Sequence
<220> FEATURE:
<223> OTHER INFORMATION: A synthetic oligonucleotide primer comprising
      human sequence.

<400> SEQUENCE: 33

```
tggaggacag aggaaaggga                                             20
```

<210> SEQ ID NO 34
<211> LENGTH: 26
<212> TYPE: DNA

-continued

```
<213> ORGANISM: Artificial Sequence
<220> FEATURE:
<223> OTHER INFORMATION: A synthetic oligonucleotide probe comprising
      human sequence.

<400> SEQUENCE: 34
agatgcagcc agttcagatc ttcccg                                          26

<210> SEQ ID NO 35
<211> LENGTH: 434
<212> TYPE: DNA
<213> ORGANISM: Homo sapiens

<400> SEQUENCE: 35
ttgagctgca ggttgaatcc ggggtgcctt taggattcag caccatggcg gaagacatgg     60
agaccaaaat caagaactac aagaccgccc cttttgacag ccgcttcccc aaccagaacc    120
agactagaaa ctgctggcag aactacctgg acttccaccg ctgtcagaag gcaatgaccg    180
ctaaaggagg cgatatctct gtgtgcgaat ggtaccagcg tgtgtaccag tccctctgcc    240
ccacatcctg ggtcacagac tgggatgagc aacgggctga aggcacgttt cccgggaaga    300
tctgaactgg ctgcatctcc ctttcctctg tcctccatcc ttctcccagg atggtgaagg    360
gggacctggt acccagtgat ccccacccca ggatcctaaa tcatgactta cctgctaata    420
aaaactcatt ggaa                                                      434

<210> SEQ ID NO 36
<211> LENGTH: 46
<212> TYPE: DNA
<213> ORGANISM: Artificial Sequence
<220> FEATURE:
<223> OTHER INFORMATION: A synthetic oligonucleotide template having no
      significant homology with human sequence.

<400> SEQUENCE: 36
ggtcacagac gggaagatct gaactggctg catcttttct cccagg                    46
```